(12) United States Patent
Bordoloi Gurunath et al.

(10) Patent No.: US 11,911,273 B2
(45) Date of Patent: *Feb. 27, 2024

(54) PROSTHETIC HEART VALVE WITH COLLAPSIBLE HOLDER

(71) Applicant: Edwards Lifesciences Corporation, Irvine, CA (US)

(72) Inventors: Ankita Bordoloi Gurunath, Irvine, CA (US); Derrick Johnson, Orange, CA (US); Brian S. Conklin, Orange, CA (US); Myron Howanec, Jr., Corona, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 754 days.

This patent is subject to a terminal disclaimer.

(21) Appl. No.: 17/067,598

(22) Filed: Oct. 9, 2020

(65) Prior Publication Data
US 2021/0022862 A1  Jan. 28, 2021

Related U.S. Application Data

(63) Continuation of application No. 15/963,311, filed on Apr. 26, 2018, now Pat. No. 10,799,353.
(Continued)

(51) Int. Cl.
*A61F 2/24* (2006.01)
*A61M 25/00* (2006.01)

(52) U.S. Cl.
CPC .......... *A61F 2/2439* (2013.01); *A61F 2/2412* (2013.01); *A61F 2220/0075* (2013.01); *A61M 2025/0096* (2013.01)

(58) Field of Classification Search
CPC ............................ A61F 2/2427; A61F 2/2439
See application file for complete search history.

(56) References Cited

U.S. PATENT DOCUMENTS

| 3,143,742 A | 8/1964 | Cromie |
| 3,320,972 A | 5/1967 | High et al. |

(Continued)

FOREIGN PATENT DOCUMENTS

| EP | 0125393 A1 | 11/1984 |
| EP | 0143246 A2 | 6/1985 |

(Continued)

*Primary Examiner* — Ashley L Fishback
(74) *Attorney, Agent, or Firm* — Guy Cumberbatch

(57) ABSTRACT

A prosthetic heart valve holder system includes a prosthetic heart valve having a base at an inflow end, a plurality of commissure posts extending from the base toward an outflow end, and valve leaflets secured to the commissure posts to permit flow through the heart valve. A deflector is provided at the outflow end having a central hub and a plurality of arms extending from the central hub secured to and covering the tips of respective commissure posts. A valve support body is secured to the base and a post connects the valve support body to the hub of the deflector. The plurality of arms are sufficiently collapsible such that, in a first position, free ends of the arms are located axially between the hub and the valve support body to prevent suture looping during an implant procedure, and in a second position, the hub is located axially between the free ends of the arms and the valve support body to permit removal of the deflector from the outflow side of the valve, through the valve leaflets, to the inflow side of the valve.

20 Claims, 21 Drawing Sheets

Related U.S. Application Data

(60) Provisional application No. 62/491,998, filed on Apr. 28, 2017.

(56) References Cited

U.S. PATENT DOCUMENTS

| | | | |
|---|---|---|---|
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,487,760 A | 1/1996 | Villafana |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson, IV et al. |
| 6,409,674 B1 | 6/2002 | Brockway et al. |
| 6,425,916 B1 | 7/2002 | Garrison et al. |
| 6,440,164 B1 | 8/2002 | DiMatteo et al. |
| 6,442,413 B1 | 8/2002 | Silver |
| 6,454,799 B1 | 9/2002 | Schreck |
| 6,458,153 B1 | 10/2002 | Bailey et al. |

(56) References Cited

U.S. PATENT DOCUMENTS

| | | |
|---|---|---|
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,645,143 B2 | 11/2003 | VanTassel et al. |
| 6,652,464 B2 | 11/2003 | Schwartz et al. |
| 6,652,578 B2 | 11/2003 | Bailey et al. |
| 6,675,049 B2 | 1/2004 | Thompson et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,741,885 B1 | 5/2004 | Park et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,795,732 B2 | 9/2004 | Stadler et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,895,265 B2 | 5/2005 | Silver |
| 6,908,481 B2 | 6/2005 | Cribier |
| 6,939,365 B1 | 9/2005 | Fogarty et al. |
| 6,964,682 B2 | 11/2005 | Nguyen-Thien-Nhon et al. |
| 7,011,681 B2 | 3/2006 | Vesely |
| 7,018,404 B2 | 3/2006 | Holmberg et al. |
| 7,025,780 B2 | 4/2006 | Gabbay |
| 7,033,322 B2 | 4/2006 | Silver |
| 7,052,466 B2 | 5/2006 | Scheiner et al. |
| 7,070,616 B2 | 7/2006 | Majercak et al. |
| 7,082,330 B2 | 7/2006 | Stadler et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,416,530 B2 | 8/2008 | Turner et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,621,878 B2 | 11/2009 | Ericson et al. |
| 7,871,432 B2 * | 1/2011 | Bergin .................. A61F 2/2427 623/2.11 |
| 7,916,013 B2 | 3/2011 | Stevenson |
| 7,998,151 B2 | 8/2011 | St. Goar et al. |
| 8,066,650 B2 | 11/2011 | Lee et al. |
| 8,248,232 B2 | 8/2012 | Stevenson et al. |
| 8,253,555 B2 | 8/2012 | Stevenson et al. |
| 8,340,750 B2 | 12/2012 | Prakash et al. |
| 8,401,659 B2 | 3/2013 | Von Arx et al. |
| 8,454,684 B2 | 6/2013 | Bergin et al. |
| 8,529,474 B2 | 9/2013 | Gupta et al. |
| 8,622,936 B2 | 1/2014 | Schenberger et al. |
| 9,101,264 B2 | 8/2015 | Acquista |
| 9,101,281 B2 | 8/2015 | Reinert et al. |
| 9,693,862 B2 | 7/2017 | Campbell et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0125805 A1 | 7/2003 | Johnson et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0010296 A1 | 1/2004 | Swanson et al. |
| 2004/0019374 A1 | 1/2004 | Hojeibane et al. |
| 2004/0027306 A1 | 2/2004 | Amundson et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0228493 A1 | 10/2005 | Bicer |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |

(56) References Cited

U.S. PATENT DOCUMENTS

| | | |
|---|---|---|
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0046040 A1 | 2/2008 | Denker et al. |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0192591 A1 | 7/2009 | Ryan et al. |
| 2009/0192599 A1 | 7/2009 | Lane et al. |
| 2010/0004739 A1* | 1/2010 | Vesely .................... A61F 2/243 623/2.11 |
| 2010/0049313 A1 | 2/2010 | Alon et al. |
| 2010/0145438 A1 | 6/2010 | Barone |
| 2010/0256723 A1 | 10/2010 | Murray |
| 2012/0123284 A1 | 5/2012 | Kheradvar |
| 2012/0296382 A1 | 11/2012 | Shuros et al. |
| 2013/0144379 A1 | 6/2013 | Najafi et al. |
| 2014/0039609 A1* | 2/2014 | Campbell ............. A61F 2/0095 623/2.11 |
| 2014/0128964 A1 | 5/2014 | Delaloye |
| 2014/0188221 A1 | 7/2014 | Chung et al. |
| 2014/0364707 A1 | 12/2014 | Kintz et al. |
| 2015/0045635 A1 | 2/2015 | Tankiewicz et al. |
| 2016/0045316 A1 | 2/2016 | Braido et al. |
| 2019/0321170 A1 | 10/2019 | Green et al. |

FOREIGN PATENT DOCUMENTS

| | | | |
|---|---|---|---|
| SU | 1116573 A1 | 7/1985 | |
| SU | 1697790 A1 | 12/1991 | |
| WO | 9213502 A1 | 8/1992 | |
| WO | 9742871 A1 | 11/1997 | |

* cited by examiner

PROSTHETIC HEART VALVE WITH COLLAPSIBLE HOLDER

CROSS-REFERENCE TO RELATED APPLICATIONS

This application is a continuation of U.S. application Ser. No. 15/963,311, filed Apr. 26, 2018, now U.S. Pat. No. 10,799,353, which claims the benefit of U.S. Application No. 62/491,998, filed Apr. 28, 2017, the entire contents all of which incorporated by reference herein for all purposes.

BACKGROUND

Field

The present disclosure generally concerns medical devices, deployment mechanisms, and methods for deploying such medical devices. More specifically, the disclosure relates to surgical replacement of heart valves that have malformations and/or dysfunctions. Embodiments of the invention relate to holders for facilitating the implantation of prosthetic heart valves at such native heart valves sites, for example, for a mitral valve replacement procedure. Embodiments of the invention also relate to methods of using the holders to facilitate implantation of prosthetic heart valves.

Description of Related Art

Referring first to FIG. 1, the human heart is generally separated into four pumping chambers which pump blood through the body. Each chamber is provided with its own one-way exit valve. The left atrium receives oxygenated blood from the lungs and advances the oxygenated blood to the left ventricle through the mitral (or bicuspid) valve. The left ventricle collects the oxygenated blood from the left atrium and pushes it through the aortic valve to the aorta, where the oxygenated blood is then distributed to the rest of the body. Deoxygenated blood from the body is then collected at the right atrium and advanced to the right ventricle through the tricuspid valve. The right ventricle then advances the deoxygenated blood through the pulmonary valve and the pulmonary artery to the lungs to again supply the blood with oxygen.

Each of the valves associated with the chambers of the heart are one-way valves that have leaflets to control the directional flow of the blood through the heart, and to prevent backflow of the blood into other chambers or blood vessels that are upstream of the particular chamber. The valves are each supported by an annulus having a dense fibrous ring attached either directly or indirectly to the atrial or ventricular muscle fibers. When a valve become diseased or damaged, leakage or regurgitation may occur, where some of the blood travels back upstream through the diseased or damaged valve, and the efficiency and/or general functionality of the heart may be compromised.

Various surgical techniques can be performed to repair or replace a diseased or damaged valve. In some valve replacement procedures, the leaflets of the diseased or damaged native valve are first removed to prepare the valve annulus for receiving the prosthetic valve. FIG. 2 shows an example of one type of popular prosthetic valve 1 that is a tissue-type bioprosthetic valve generally constructed with natural-tissue valve leaflets 2, made for example, from porcine tissue or bovine pericardium, or from artificially synthesized tissue, that are mounted on a surrounding valve stent structure 3. The shape and structure of the leaflets 2 are supported by a number of commissure posts 4 positioned circumferentially around the valve stent structure 3. In these valves, a biocompatible cloth-covered suture or sewing ring 5 can also be provided on an inflow end of the stent structure 3 of the valve 1, for attachment to the native valve annulus. Such prosthetic valves function much like natural human heart valves, where the leaflets coapt against one another to effect the one-way flow of blood.

When implanting a tissue type prosthetic valve as described above at a native valve annulus, a number of sutures may be involved in the attachment process, many of which may be pre-installed for providing a track on which the valve is advanced along, or "parachuted" down, until it is properly positioned at the implant site. Additional attachment sutures may also be applied between the prosthetic valve and the heart walls after proper placement, to securely attach or hold the valve implant in place. Meanwhile, in some cases, the prosthetic valves are implanted through small access channels using one of various minimally invasive surgical procedures, where visibility at the implant site may be impeded or obstructed. In addition, depending on the direction of implantation, for example, with some mitral valve replacement procedures, commissure posts of the stent or frame, or other portions of the prosthetic valve may be pointed distally and located on a blind side of the valve.

Each of the above factors may lead to tangling of the pre-installed sutures with the valve prosthesis, most commonly with the commissure posts of the frame, since they provide a protrusion on which the sutures can easily loop around and tangle. This type of entanglement of sutures with prosthetic valves is referred to as "suture looping," which specifically refers to instances where a pre-installed suture is inadvertently wrapped around one or more of the commissure post tips, where it can then migrate towards and damage the leaflets or interfere with proper leaflet coaptation or other valve operation when the sutures are tightened or secured, resulting in improper valve operation. In some cases, such tangling may not be apparent to the practitioner at the time of implantation, and will only be revealed some time later when valve operation is observed to be improper or other complications arise in the patient, in which case, it may be necessary to initiate another procedure to repair or replace the prosthetic valve.

SUMMARY

Attempts have been made to resolve the problem of suture looping, some of which revolve around the holders which hold the prosthetic valves when they are delivered to the native valve annulus. In one example, a holder has a mechanism that urges the commissure posts of the prosthetic valve radially inward during delivery, so that the ends of the commissure posts are pointed inwards, to reduce the possibility of sutures catching against or looping around them. After the valve prosthesis is delivered to the implant site, the holder is removed, releasing and expanding the commissure posts to their original positions. However, although the commissure posts are biased inwardly during delivery, since the ends of the commissure posts remain free, these holders have not been fully effective in eliminating instances of suture looping.

Meanwhile, Edwards Lifesciences has developed another valve holder system, known as Tricentrix®, specifically for use in mitral valve replacement procedures to protect the valve from suture looping during valve implantation. The system includes monofilament deflection sutures that attach to both the holder and pairs of commissures of the prosthetic valve, so that the sutures run across the outflow end of the valve between the ends of the commissures. When the holder is actuated, a central post extends distally through the prosthetic valve between the leaflets and pushes against the sutures in the middle of the valve between the commissures, pushing the sutures distally and causing an angled tent-like or umbrella shape of sutures. The pressure on the sutures deflects the commissures slightly inward, while also forming the angled umbrella shape of the sutures that slope outwardly and downwardly from the central post to the commissure posts. These angled surfaces deflect away from the prosthetic valve any other sutures, such as the pre-installed attachment sutures, mentioned above, that might otherwise engage and be looped around a commissure or valve leaflet.

Other holders have also been developed in an attempt to further reduce instances of suture looping. However, some of these holders are very complex, for example, incorporating various rotary and advancement mechanisms in addition to the original hold and release mechanisms, such that a number of additional steps must be taken by the practitioner to operate the holders correctly. Many of these holders have proven to be too complicated and/or prone to user error, such as a failure to execute all deployment steps in the correct order. Consequently, when practitioners use these holders improperly, suture looping can still occur, while the implant process may also be further complicated by issues arising from user error.

In addition to the above, many of the newer holder designs also incorporate many additional parts that interact with one another or that must be assembled by the practitioner or other end user, which may also lead to additional complications. For example, where additional parts must be threaded into one another, cross-threading can occur when the threads of the various parts are inadvertently misaligned. This and/or other interactions between the additional parts may lead to increased possibility of the holder being damaged or breaking, and of loose fragments being generated.

Features of the invention provide for new holder systems and methods of using the holder systems, which reduce or eliminate the occurrence of suture looping or other damage to the prosthetic valves during implantation. Operation of the holders is also simplified, where the additional features of the holders can be pre-deployed or integrated for deployment or actuation automatically when performing existing steps already well-known by users, thereby reducing or eliminating mistakes caused by user error and increasing patient safety. The holders can also have a reduced number of parts and/or provide for integrated alignment features or other safety features, so that cross-threading or other damaging interactions between parts can also be prevented. These holders can also be made at similar or reduced costs compared to existing holders. In addition, reducing the number of deployment steps reduces the time to complete the surgical procedure, and reduces the complexity of training, or retraining, needed to learn the procedure.

In one embodiment of the invention, a prosthetic heart valve holder system includes a prosthetic heart valve having an inflow end and an outflow end and a flow axis therethrough. The heart valve further has a base at the inflow end, a plurality of commissure posts extending from the base toward the outflow end and circumferentially spaced around the flow axis, and valve leaflets secured to the commissure posts to permit flow through the heart valve, each commissure post having a tip at the outflow end. The valve holder system further includes a deflector at the outflow end having a central hub and a plurality of arms extending from the central hub. A first end of each of the arms are secured to the central hub and a second end of each of the arms are secured to and cover a tip of a respective commissure post of the plurality of commissure posts. A valve support body is secured to the base at the inflow end and a post extends from the valve support body at the inflow end of the heart valve, through the valve leaflets, to the hub of the deflector at the outflow end. The plurality of arms of the deflector are sufficiently collapsible such that, in a first position, the second end of each of the plurality of arms is located axially between the hub and the valve support body such that the deflector prevents suture looping during an implant procedure. In a second position, the hub is located axially between the second end of each of the plurality of arms of the deflector and the valve support body to permit removal of the deflector from the outflow side of the valve, through the valve leaflets, to the inflow side of the valve without damaging the valve leaflets after detachment of the deflector arms from the tips of the commissures.

In a preferred embodiment of the prosthetic heart valve system, the plurality of commissures posts is at least three commissure posts and the plurality of arms of the deflector is at least three arms. In other embodiments, the post is a solid pin and the post may be molded or press-fit to the deflector. In a further embodiment, the deflector and the valve support may be permanently fixed a first distance apart from one another by the post. The prosthetic heart valve, the deflector and the valve support body may also be mounted in a package in the first position.

In a further preferred embodiment of the invention, the deflector is a monolithic body of flexible material. The flexible material preferably has a durometer in the range of Shore A30 to Shore A70. In an alternative embodiment, each of the plurality of arms has a transversely extending notch that forms a living hinge. In other embodiments, a layer of material that is resistant to viscoelastic stress relaxation, such as a layer of cloth, is embedded in or overmolded to the arms of the deflector. Preferably the plurality of arms of the deflector are held taut between the central hub and the plurality of commissure posts. In another embodiment, the second end of each arm is a channel member that extends over the top and three sides of the tip of the respective commissure post.

In a further embodiment, the prosthetic heart valve holder system includes an adaptor configured to be detachably connected to the valve support body on an opposite side of the valve support body from the deflector. The adaptor can be detachably connected to the valve support body by a suture.

A plurality of additional sutures can be routed from the opposite side of the valve support body, through respective commissure posts to the tips of the commissure posts, through respective deflector arms, back to the tips and back down the commissure posts, through the valve support body again and fixed to the opposite side of the valve support body. In a preferred embodiment, each of the plurality of additional sutures has a portion that is placed over a gap on the opposite side of the valve support body to permit the portions to be all cut in a single action. The adaptor may include a suture shield mounted over the gap to protect the suture portions from premature cutting until the adapter is detached from the valve support body. A handle may also be detachably connectable to the adaptor from the opposite side of the valve support body from the deflector.

In another alternative embodiment, a prosthetic heart valve holder includes a deflector having a central hub and a plurality of arms extending from the central hub, each of the plurality of arms having a first end secured to the central hub and a free second end radially outward from the hub, the valve holder further includes a valve support body and a post extending from the valve support body to the hub of the deflector. The plurality of arms of the deflector are sufficiently collapsible such that, in a first position, the second end of each of the plurality of arms is located axially between the hub and the valve support body, and in a second position, the hub is located axially between the second end of each of the plurality of arms of the deflector and the valve support body.

In a further embodiment, the plurality of arms of the deflector are sufficiently collapsible such that, in a first position, the hub is a first axial distance from the valve support body and the second end of each of the plurality of arms extends an axial distance less than the first axial distance from the valve support body and in a second position, the second end of each of the plurality of arms of the deflector is at an axial distance greater than the first axial distance.

According to embodiments of the invention, holders for prosthetic valve delivery reduce or eliminate occurrences of suture looping and/or other damage to the valves when the valves are implanted, while the mechanisms for deploying these features are integrated into the holders in a way that make it easier for end users to use and deploy.

BRIEF DESCRIPTION OF THE DRAWINGS

Further features and advantages of the invention will become apparent from the description of embodiments using the accompanying drawings. In the drawings.

DETAILED DESCRIPTION

Disclosed herein are various valve holders for assisting in the delivery and implantation of prosthetic heart valves at an implant site, and methods for preparing the prosthetic heart valves for such procedures. Embodiments of the valve holders reduce occurrences of various complications that may arise during implantation, while remaining simple for end users to use. By providing these improved valve holders, damage to the prosthetic valves during surgical procedures can be reduced, and additional costs for extended or additional procedures and replacement valves can be avoided.

The valve holders disclosed herein are particularly useful for avoiding suture looping and other valve damage during advancement of the prosthetic valves to the implant sites as well as during final suturing of the valves at the native valve annulus. In procedures where commissure posts of the prosthetic valve point distally, for example, in many mitral valve replacement procedures, the commissure posts point in the direction of valve advancement and may be more prone to suture looping or other entangling. In these cases, valve holders according to embodiments of the invention provide deflectors that deflect the pre-installed sutures away from the prosthetic valve. In some embodiments, the valve holder system has a deflector that is pre-deployed without requiring any action by the surgeon or operating room staff and is ready for delivery to the native valve annulus upon removal of the packaging. Upon securement of the prosthetic heart valve to the annulus, the deflector is collapsible to permit it to be pulled through the leaflets without causing any damage when the holder is removed from the prosthetic valve. In other embodiments, the surgeon or operating room staff may effect automatic deployment or actuation of the respective valve holders to their deployed positions, using steps that are already associated with handling of existing valve holders. As with the pre-deployed system, upon securement of the prosthetic heart valve to the native valve annulus, the deflector is collapsible to permit it to be pulled through the leaflets without causing any damage when the holder is removed from the prosthetic valve. In this fashion, ease of use of the below described valve holders can be maintained, while user error can be minimized.

Figure 6:
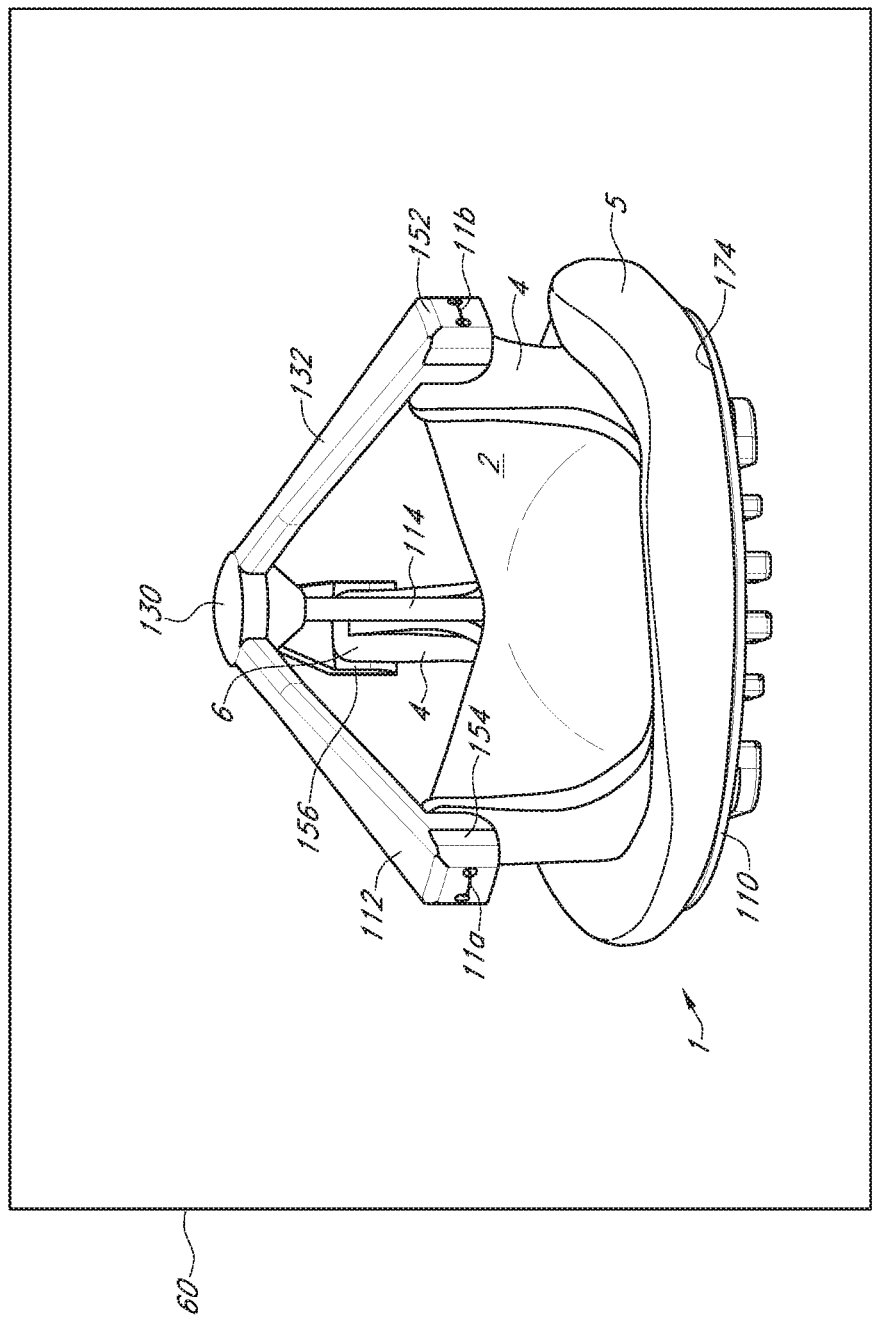
FIG. 6 shows a perspective view of the valve holder of FIG. 3 with a prosthetic heart valve.

With reference to FIGS. 3-6, an embodiment of the prosthetic valve holder system of the present invention includes a valve holder 100 that includes a valve support body 110 attached to a deflector 112 by a central post 114, an adapter 116, an optional handle 118, and a prosthetic heart valve 1. According to an embodiment of the invention, the prosthetic heart valve holder system is provided to the surgical team in a pre-deployed arrangement with the prosthetic valve 1 captured between the valve support body 110 and the deflector 112, as shown in FIG. 6. The post 114 extends through the center of the prosthetic valve through the leaflets 2 and between the support body 110 and the deflector 112. According to this embodiment, the system does not need any steps to activate the suture looping protection, and can be used with or without the handle 118.

Figure 7:
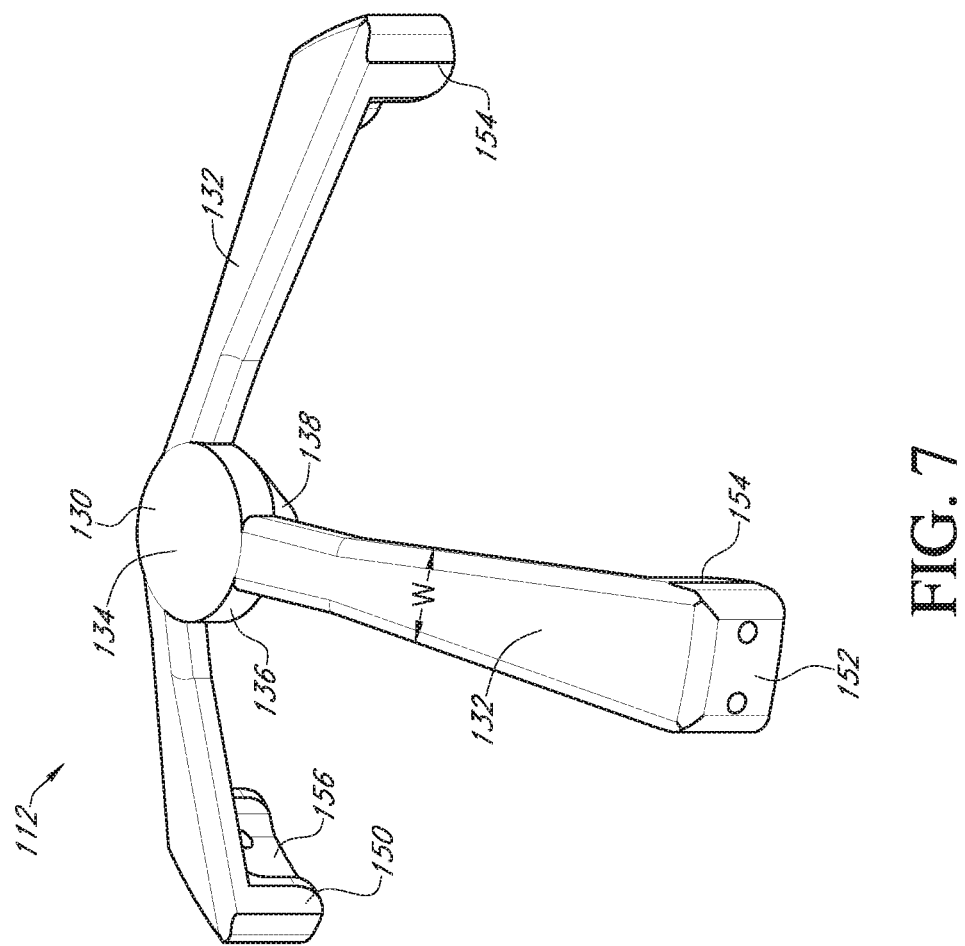
FIG. 7 shows a top perspective view of a deflector of the valve holder of FIG. 3.
Figure 8:
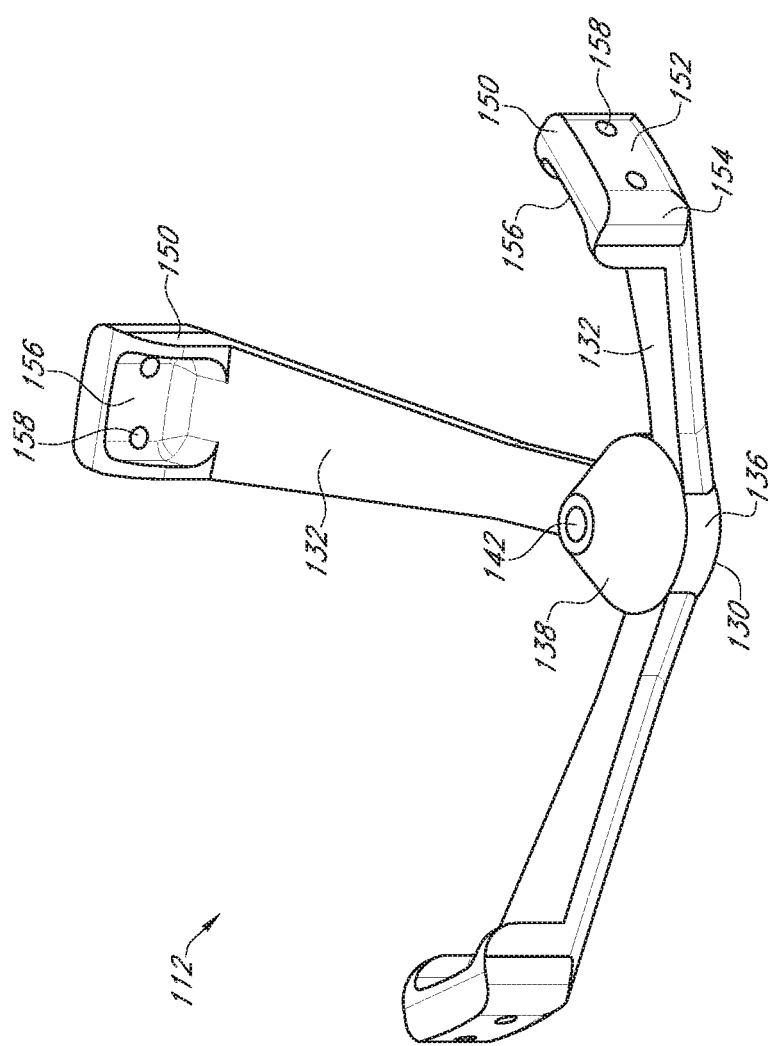
FIG. 8 shows a bottom perspective view of the deflector of FIG. 3.

With reference to FIGS. 7 and 8, the deflector 112 includes a central hub 130 and three generally radially extending arms 132. Preferably, the deflector is a monolithic body made of a highly flexible material which allows the arms to easily fold when the deflector is pulled through the leaflets of the prosthetic valve after attachment of the valve to the native valve annulus and during release of the holder.

Preferred materials for the deflector are rubber, such as a soft silicone rubber, a soft flexible polymer, or other materials having a durometer in the range of Shore A30-A70, or preferably about Shore A50.

Additionally, the deflector may be overmolded with a cloth, fabric or other thin mesh material to give the arms strength and resistance to viscoelastic stress relaxation, yet maintain the flexibility of the deflector to permit removal through the valve leaflets. The cloth, fabric or mesh may be a single piece embedded in the deflector across the central hub and the three arms or may be multiple pieces.

The central hub 130 of the deflector has a smooth convexly curved top surface 134, a cylindrical side surface 136, and a truncated conical bottom surface 138 that narrows in a direction away from the top surface. The curved top surface 134 is for deflecting away from the leaflets any pre-installed attachment sutures during installation of the prosthetic valve. The conical bottom surface 138 provides a tapered surface to gradually spread the leaflets during retraction and removal of the deflector through the leaflets after the valve has been attached. At the truncated tip of the conical bottom surface, an opening to a bore 142 is provided for receipt of one end of the post 114.

Extending radially and downwardly away from the central hub 130 are the three arms 132. One end of each arm is secured to the cylindrical side surface of 136 of the central hub. The other end of each arm is configured to mount over a tip 6 of a respective commissure post 4 of the prosthetic valve (see FIG. 2). Accordingly, the length of each arm should be sufficient to extend from the central hub to the commissure post and over the commissure post. Preferably, the arms are held taut between the hub and the posts to cause any pre-installed assembly sutures to slide down the deflector during installation of the prosthetic valve, thus preventing suture looping. In addition, the arms may be used to also deflect or urge the commissure posts inward.

To improve the connection between the arms 132 of the deflector 112 and the commissure posts 4, the radially outer end portion of each arm forms a channel member 150 that extends down from the end of each arm. The channel member 150 has an end wall 152 and two side flanges 154 extending radially inward from the end wall to form a channel 156 to receive a tip 6 of a commissure post 4. The end wall 152 of each channel member is thickened and includes two suture holes 158 extending through the end wall into the channel 156. Preferably, the end wall of the deflector is wider than the width of the tip of the commissure post and the side flanges cover a substantial portion of the sides of the tip so as to surround the top and outside of the tip, thereby offering excellent protection against suture looping.

To improve the flexibility of the arms of the deflector, the width (w) of each arm, measured across the top surface of the arm, is gradually tapered or narrowed beginning from a location near the channel member 150 of the arm to a location near the central hub 130.

Figure 9:
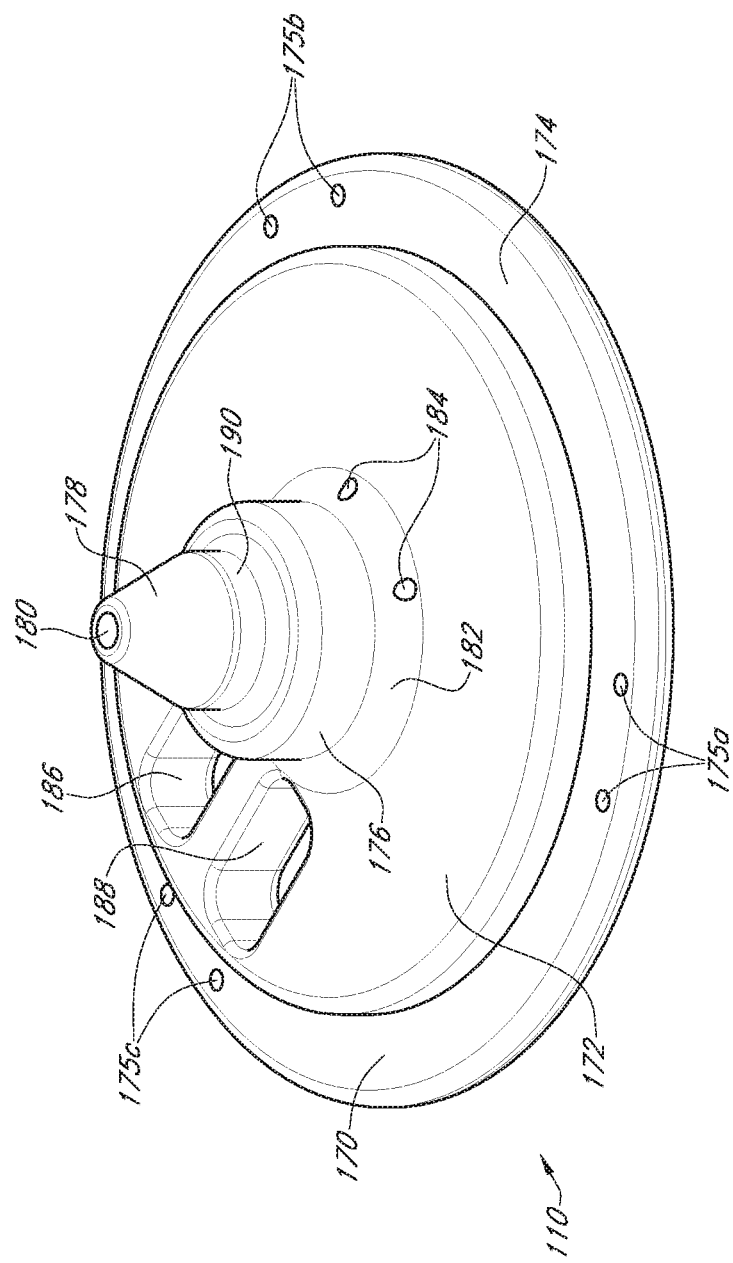
FIG. 9 shows a top perspective view of a valve support body of the valve holder of FIG. 3.

With reference to FIG. 9, the valve support body 110 is in the form of a circular disk 170 having a raised central platform 172 that is smaller in diameter than the circular disk 170. The central platform 172 is concentric to the circular disk and therefore an outer circumferential portion of the circular disk forms an annular base surface 174 that can receive and be attached to the suture or sewing ring 5 of the prosthetic heart valve (see FIG. 2). The annular base surface 174 is provided with three pairs of suture holes 175a, 175b, 175c through the valve support body, each pair being configured to be aligned with a respective commissure post 4 of the prosthetic heart valve in order to suture the valve 1 to the support body 110.

Projecting up from the raised central platform 172 of the support body is a cylindrical base member 176 centrally located on the platform 172. Furthermore, projecting up from the base member 176 is a truncated conical member 178 having a conical surface that narrows in a direction away from base member 176. The narrowing will assist in preventing any interference between the valve support body 110 and the prosthetic valve leaflets 3 during the surgical procedure. At the truncated tip of the conical member 178, an opening to a bore 180 is provided for receipt of an end of the post 114 (see FIG. 3).

In one embodiment, the post is molded to the conical member 178 of the support body 110 and to the truncated tip of the deflector 112. Other methods of attachment may be used such as a press fit, but the attachment should be secure to prevent detachment during removal of the valve support body 110 and deflector 112 from the prosthetic valve after completion of the surgical procedure. In addition, the post has a small diameter such that it can pass through a central hole 7 of coapted leaflets of the valve, without significantly deforming the leaflets.

A beveled surface 182 is located between the central platform 172 and the base member 176. In an embodiment, a pair of suture holes 184 are located next to each other through the beveled surface in order to provide a securement point for the adapter 116 (see FIG. 3) to the support body 110. It will be appreciated that the suture holes 184 may be placed at other locations of the support body as deemed necessary. Passing through the central platform are also a pair of tool openings 186 such that the valve support body 110 can be grasped and positioned as needed by a surgical instrument (not shown). The openings 186 may be of any suitable shape (e.g., rectangular) to provide a rib 188 or other structure between the openings for grasping.

Figure 3:
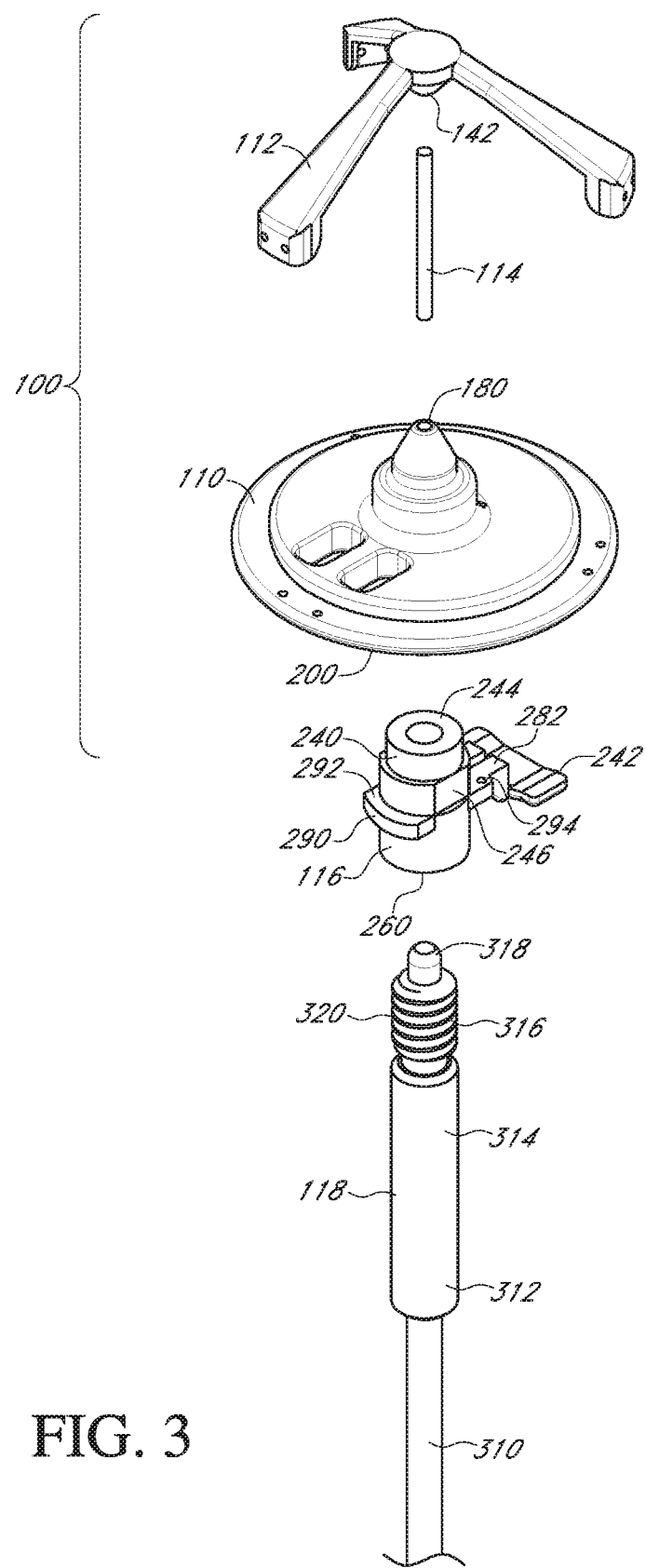
FIG. 3 shows an exploded perspective view of a valve holder, adapter and handle for a prosthetic heart valve according to an embodiment of the invention.
Figure 10:
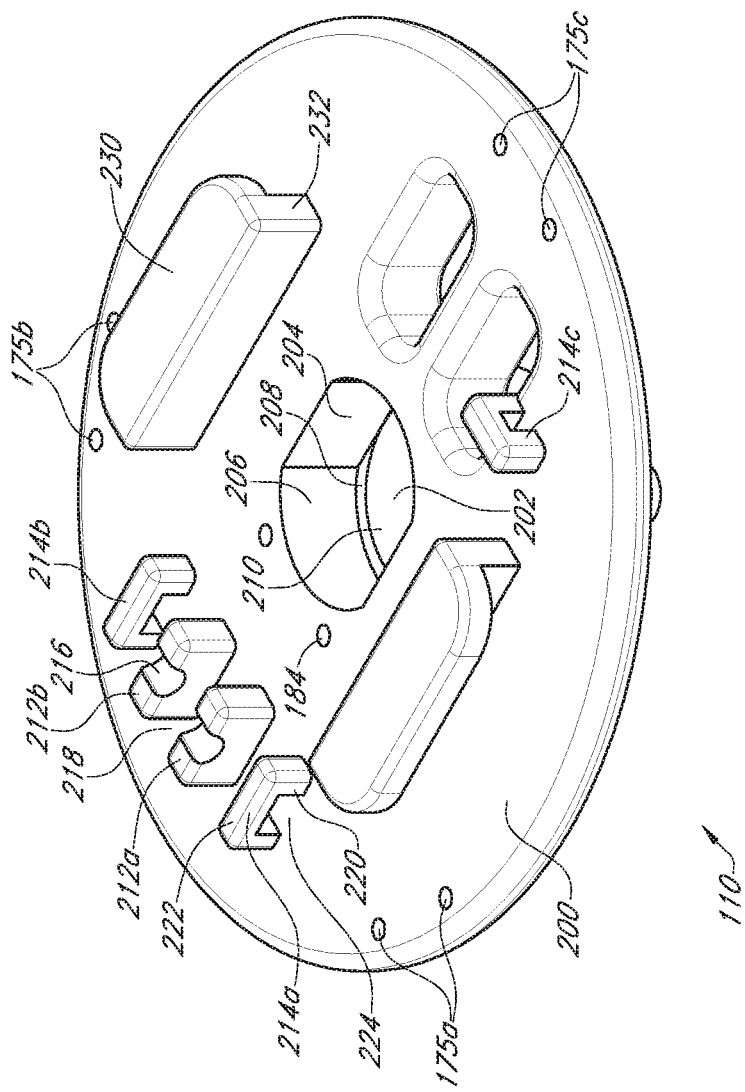
FIG. 10 shows a bottom perspective view of the valve support body of FIG. 3.

With reference to FIG. 10, the bottom side 200 of the valve support body 110 includes a central hole 202 to receive the adapter 116 (see FIG. 3). The central hole 202 includes a first axially extending hole portion having opposed flat sides 204 and opposed curved sides 206. At the end of the first axially extending hole portion, shoulders 208 are formed that serve as an abutment to a corresponding portion of the adapter 116. Extending axially further into the valve support body 110 is a second axially extending hole portion having a cylindrical inner surface 210. The second axially extending hole portion is also sized to receive a corresponding portion of the adapter, which will be described in more detail below.

Projecting from the bottom side 200 of the valve support body are a plurality of suture supports 212a, 212b and suture tunnels 214a, 214b, 214c. The suture supports 212a, 212b are rectangular blocks, each with an exposed groove surface 216. The groove is a smooth cylinder or otherwise concave surface. In an embodiment of the invention, the suture supports 212a, 212b are adjacent to each other and their grooved surfaces 216 are aligned such that multiple sutures can be laid across a gap 218 between the suture supports. As will be seen below, this will provide a single cut point to release the valve holder 100 from the prosthetic heart valve 120.

The suture tunnels 214a and 214b each have two columns 220 with an interconnecting span member 222 that together form a tunnel space 224 for receiving one or more sutures therethrough. In one embodiment, there are three support tunnels 214a, 214b, 214c, each located near a respective pair of suture holes 175a, 175b, 175c. Two of the suture tunnels 214a, 214b are located on opposite sides of and adjacent to respective suture supports 212a, 212b such that the tunnel spaces 224 are aligned with the groove surfaces 216 to provide a suture pathway across the gap 218. The third suture tunnel 214c is located next to one of the tool openings 186 and near the third pair of suture holes 175c. It will be appreciated that the number and location of suture supports and suture tunnels for routing and tying down sutures may be varied as desired. In addition, the columns 220 and span members 222 of the suture tunnels are rounded so as not to chafe or abrade the sutures and to provide secure surfaces for tying down the sutures. The valve support body 110 may be made as a single piece out of a rigid plastic material, or other material suitable to safely secure the prosthetic valve during shipment and use.

Packaging guides 230 are also provided on the valve support body 110 in order to secure the valve holder 100 and prosthetic heart valve 120 within a package for shipping. In an embodiment of the invention, the packaging guides are a pair of L-shaped support guides 232 configured to engage packaging components (not shown). A package 60 for the valve holder 110 and prosthetic valve 1 is shown schematically in FIG. 6.

With reference to FIG. 3, the adapter 116 may be employed when the surgeon prefers to use a handle to insert the prosthetic heart valve into the native valve annulus. The adapter provides an attachment mechanism to attach the handle. The adapter may also be used to provide other features, such as suture protection during the implant procedure. The adapter may be made as a single piece out of a rigid plastic material or other suitable material.

Figure 11:
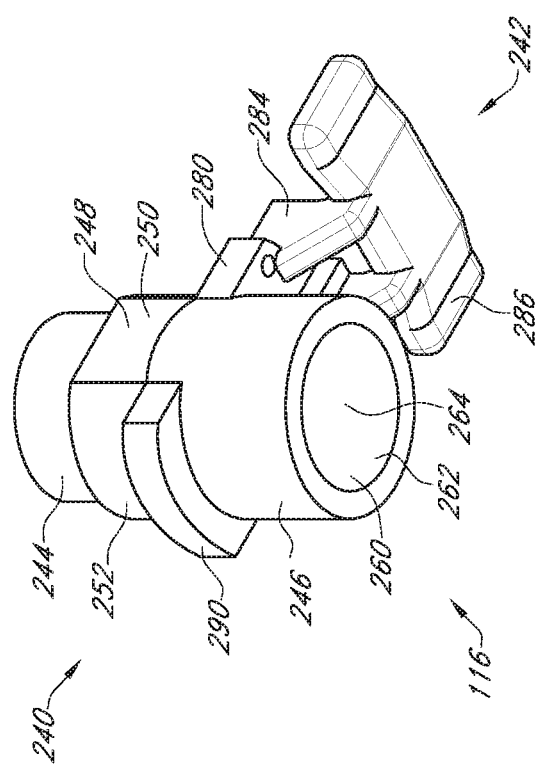
FIG. 11 shows a bottom perspective view of an adapter of the valve holder of FIG. 3.
Figure 12:
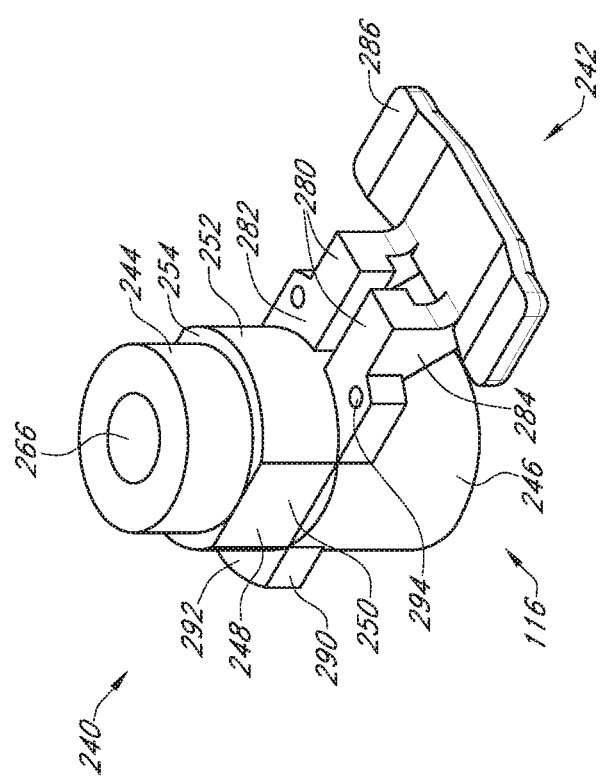
FIG. 12 shows a top perspective view of the adapter of FIG. 3.

With reference to FIGS. 11 and 12, the adapter 116 includes a post member 240 and a suture shield 242. The post member 240 has at one end a first cylindrical member 244 that is sized to fit within the cylindrical inner surface 210 of the valve support body 110. The connection may be a press fit, but the connection should not be so tight as to make it difficult to detach the adapter 116 from the valve support body 110 during the surgical procedure.

At the other end of the post member 240 of the adapter 116 is a second cylindrical member 246 that has a greater outer diameter than the first cylindrical member 244. Located between the first and second cylindrical members is an anti-rotation member 248 having opposed flat sides 250 and opposed curved sides 252. The anti-rotation member is sized to fit within the central hole 202 of the valve support body 110 and is sized to prevent or restrict rotation between the adapter 116 and the valve support body 110. On the end of the anti-rotation member 248 adjacent the first cylindrical member 244, the opposed curved surfaces 252 project to form abutments 254 that can engage the shoulders 208 in the central hole 202 of the valve support body 110. This prevents the adapter from being inserted too far into the valve support body.

The suture shield 242 extends laterally from the end of the second cylindrical member 246 adjacent to the anti-rotation member 248. The suture shield 242 includes two support arms 280 each having a flat surface 282 that can bear against the bottom side 200 of the valve support body. At the end of each support arm 280, a vertical extension member 284 is provided that projects away from the flat surface in the direction of the second cylindrical member 246. The extension members 284 support a suture cover 286 that is arranged to overlap the suture supports 212a, 212b and the suture tunnels 214a, 214b. The suture cover 286 prevents the surgeon or clinician from prematurely cutting the sutures to release the valve support body 110 from the prosthetic heart valve 120. The length and width of the suture cover 286 is preferably sufficient to cover the entire top of each of the suture supports 212a, 212b and suture tunnels 214a, 214b.

The adapter further includes a tab 290 extending laterally in an opposite direction from the suture shield 242. The tab has a flat surface 292 that, similar to the flat surfaces 282 of the suture shield, can bear against the bottom side 200 of the valve support body 110 to form a firm connection. Suture holes 294 are provided through suture shield 242 and are aligned with the suture holes 184 of the valve support body 110 so that a suture can be tied to secure the adapter 116 to the valve support body 110.

Figure 13:
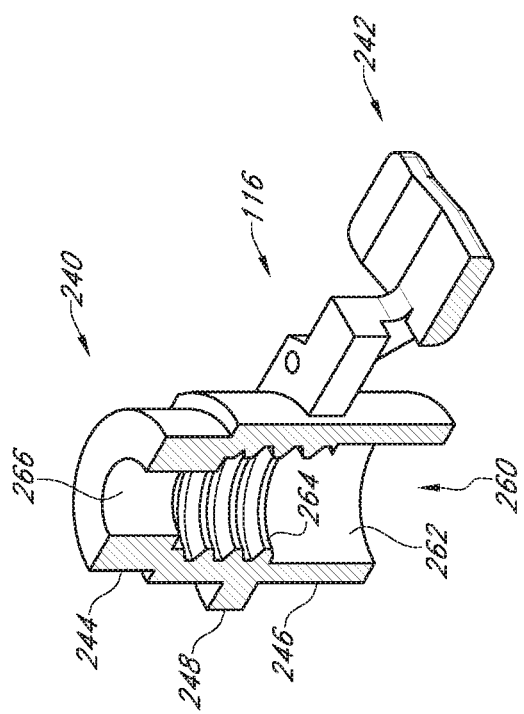
FIG. 13 shows a cross-sectional view of the adapter of FIG. 12.

With reference to FIG. 13, the post member 240 of the adapter 116 has a central bore 260 running through the second cylindrical member 246, the anti-rotation member 248 and at least a part of the first cylindrical member 244. The central bore 260 has an unthreaded portion 262 at the opening to the second cylindrical member 246. Adjacent the unthreaded portion 262 is a threaded portion 264 in the anti-rotation member 248. The first cylindrical member 244 has a reduced sized bore 266 to receive an unthreaded lead-in section 318 of the handle 118. The bore 266 is the same diameter as or a larger diameter than the lead-in section 318 to provide clearance.

With reference to FIG. 3, the handle 118 has a bendable portion 310 to permit the handle to be bent in order to access the surgical site from different directions and angles. The bendable portion 310 is secured to a rigid portion 312 that includes an unthreaded portion 314 and a threaded portion 316 closer to a tip 318 of the handle than the unthreaded portion. In an embodiment, the outer diameter of a thread 320 of the threaded portion 316 is the same as the outer diameter of the unthreaded portion 314, although the diameter may be different in other embodiments. The outer diameter of the thread 320 is the same as the inner diameter of the unthreaded portion 262 of the central bore 260 of the adapter 116. The length of the unthreaded portion 262 is several millimeters before the start of the threaded portion 204 of the central bore 260. The unthreaded portion 262 helps insure axial alignment between the threads of the adapter and the handle to prevent cross-threading.

Assembly of the prosthetic heart valve holder system of the embodiment of FIGS. 1-13 proceeds as follows. With reference to FIG. 3, one end of the central post 114 is inserted into the bore 142 of the deflector 112 and the other end of the post is inserted into the bore 180 of the valve support body 110. As mentioned earlier, the attachment of the central post to the deflector and the valve support body may be by press fit or overmolding, or any other method, such as a snap fit, that prevents the parts from being detached during the surgical procedure.

Figure 1:
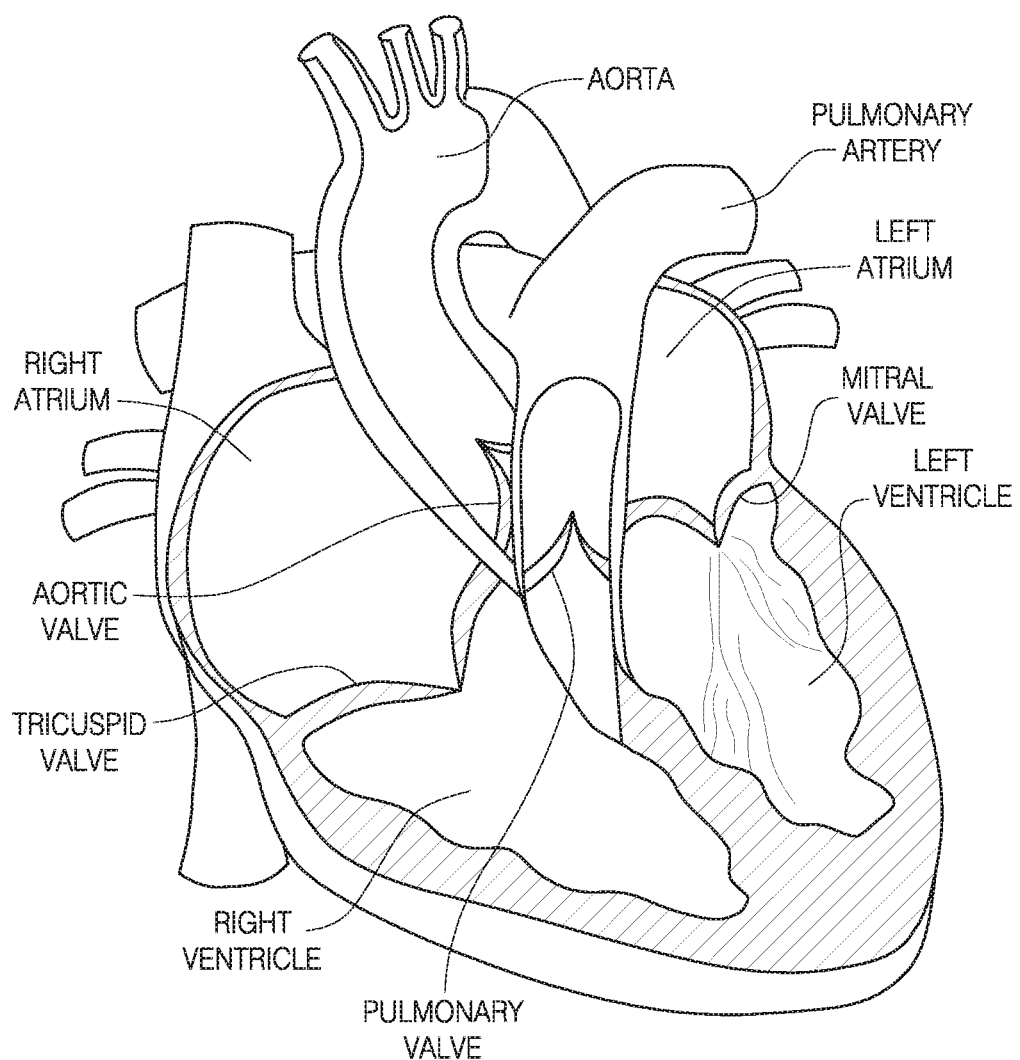
FIG. 1 shows a schematic cross-sectional view of a human heart.
Figure 2:
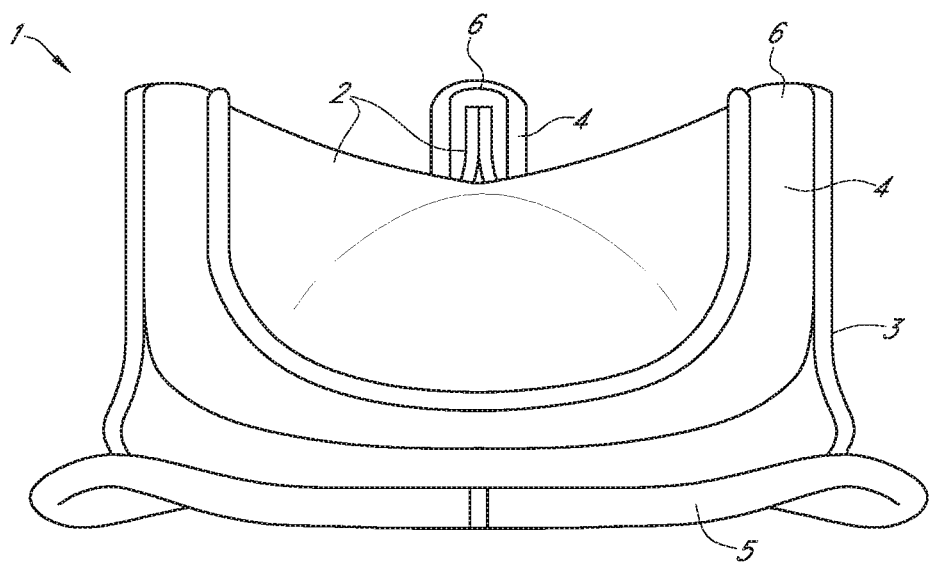
FIG. 2 shows a schematic perspective view of an example of a prosthetic valve that can be used with embodiments of the invention.
Figure 4:
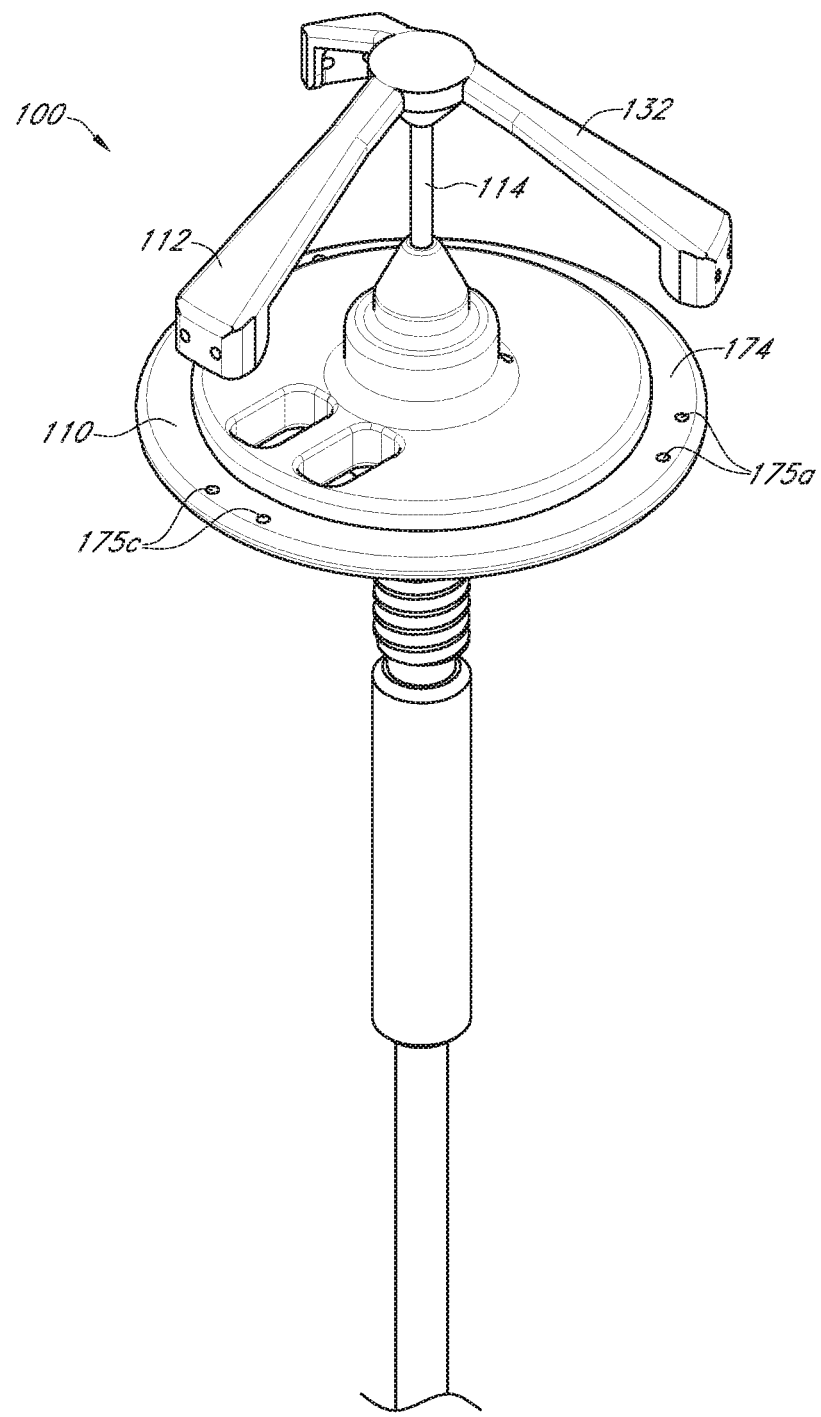
FIG. 4 shows a top perspective view of the valve holder, adapter and handle of FIG. 3 in an assembled state.
Figure 5:
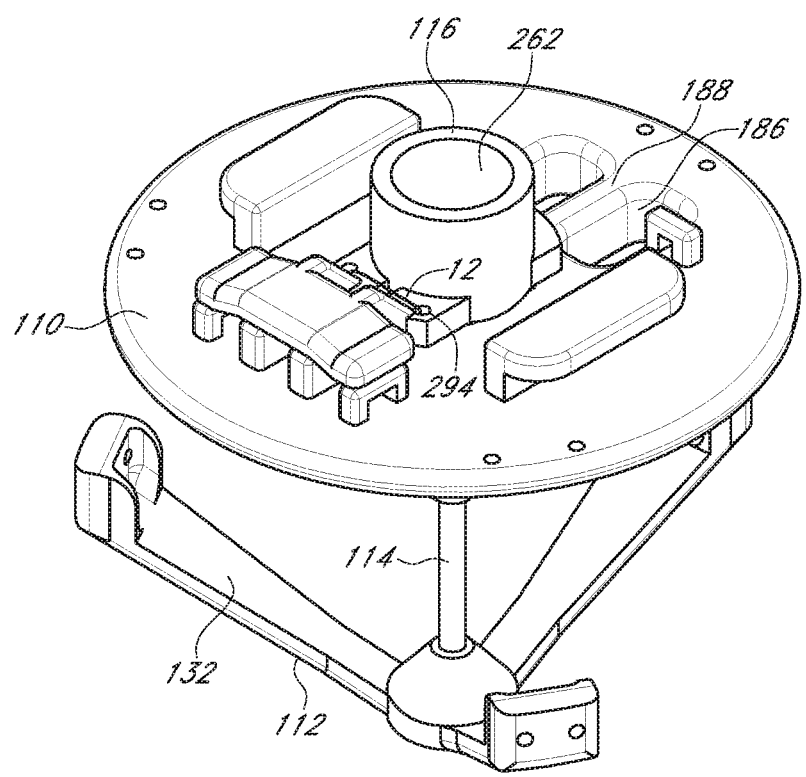
FIG. 5 shows a bottom perspective view of the valve holder and adapter of FIG. 3 in the assembled state.

The assembled valve support body 110 and deflector 112 are then attached to the prosthetic heart valve 1 (see FIGS. 2 and 4). This may be done by inserting the deflector 112 into the inflow end of the prosthetic heart valve 1. During the process the arms 132 of the deflector will engage the leaflets 2 and bend or fold inward toward the central post while the leaflets are moved out of the way to permit the deflector to pass through the leaflets to the outflow end of the prosthetic valve. The deflector 112 is pushed through the valve until the suture ring 5 of the heart valve engages the annular base surface 174 of the valve support body 110 (see assembled valve holder 100 and prosthetic valve 1 in FIG. 6).

After the suture ring 5 is mounted on the annular base surface 174, the heart valve is rotated on the base surface in order to align the three pairs of suture holes 175a, 175b, 175c of the valve support body with their respective commissure posts 4 of the prosthetic valve. Simultaneously, the deflector arms 132 are aligned with respective tips 6 of the commissure posts 4.

The deflector arms 132 are arranged over the commissure posts 4 such that the tips 6 enter the channels 156 at the outer end portion of each arm. Preferably, the end wall 152 of the deflector arm is wider than the width of the tip and the side flanges 154 cover a portion of the sides of the tip. The angle that the deflector arms 132 form with the central post 114 when mounted to the tips 6 of the commissure post is sufficient to result in the tent-like or umbrella shape, preferably about 25 to 60° such that the ends of the deflector arms attached to the commissure posts are located axially between the central hub 130 and the valve support body 110. In addition, the deflector arms are held taut by the commissure posts 4 causing the deflector to assume an angled tent-like or umbrella shape.

Figure 14:
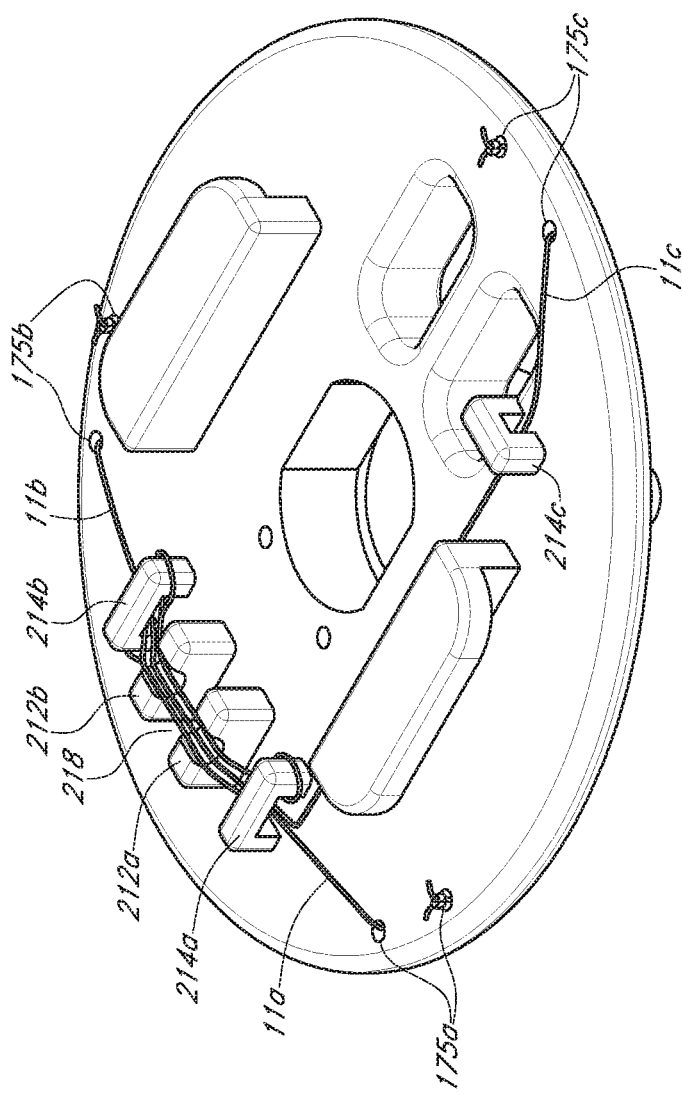
FIG. 14 shows a bottom perspective view of the valve support body of FIG. 3 with sutures.

Sutures 11 are used to attach the prosthetic valve to the support body 110 and the arms 132 of the deflector. With reference to FIG. 14, suture 11c is passed through one of the pair of suture holes 175c. The end of the suture 11c is knotted (at x) to prevent it from passing through the hole. Suture 11c is passed through the suture ring 5 and along the commissure post 4 to a location near the tip 6 (not shown). The suture 11c is threaded out of the commissure post and through one of the pair of suture holes 158 of the deflector arm to the outside of the end wall 152 and is threaded back to the tip of the commissure post through the other one of the pair of suture holes 158 and threaded back down the commissure post through the suture ring 5 and through the other one of the pair of suture holes 175c. Suture 11c is threaded through suture tunnel 214c, through suture tunnel 214a, over both suture supports 212a, 212b and tied down to suture tunnel 214b.

Sutures 11a and 11b are similarly passed through respective pairs of suture holes 175a, 175b, through the suture ring 5, up respective commissure posts 4 to the tips 6, routed out and in through respective holes 158 of the deflector arms 132 (see FIG. 6), into the tips 6 and back down the commissure posts 4 through the suture ring 5 and through the adjacent hole of the respective pair of suture holes 175a, 175b. Each suture 11a and 11b is passed through a suture tunnel 214a, 214b over both suture supports 212a, 212b and tied down to the other suture tunnel 214a, 214b. In this way, all three sutures 11a, 11b, 11c are arranged across the gap 218 between the two suture supports 212a, 212b to provide a single cut point at the completion of the surgery to release the valve holder 100 from the prosthetic valve 1.

The suture 11a, 11b, and 11c also hold the deflector arms 132 taut against the commissure posts 4. This results in the arms 132 assuming a tent-like or umbrella shape that will cause the pre-installed sutures to slide or glide off the umbrella during valve placement and thereby preventing suture looping.

When a handle for the holder is desired (see FIG. 3), the adapter 116 is attached to the valve support body 110 by inserting the post member 240 of the adapter 116 into the central hole 202 of the valve support body 110 (see FIG. 10). In particular, the post member 248 is inserted until the first cylindrical member 244 and the anti-rotation member 248 of the post member are fully inserted into the central hole of the valve support body 110. Preferably, the flat surfaces 282 of the suture shield 242 and the flat surface 292 of the tab 290 abut the bottom side 200 of the valve support body 110. Finally, a suture 12 is threaded through suture holes 294 of the suture shield and suture holes 184 in the support body 110 to secure the adapter 116 to the support body (see FIG. 3).

The handle 118 is attached to the adapter 116 by guiding the threaded portion 316 of the handle into the central bore 260 of the adapter 116. The unthreaded portion 262 of the central bore (see FIG. 5) will act as a guide to axially align the handle 118 and the central bore 260 of the adapter to permit the handle to be screwed in without cross-threading.

During the surgical procedure, the handle 118 may be used to guide the prosthetic heart valve holder system to the native valve annulus. Examples of such a procedure for installing a new mitral valve is described in U.S. Patent Application Publication No. 2002/0013621, and U.S. Pat. No. 6,966,925, both incorporated herein by reference.

In order to secure the prosthetic valve to the native valve annulus, a plurality of sutures can be pre-installed within the mitral valve annulus. The sutures are then brought outside the body and passed through the suture ring 5 of the prosthetic valve 1 of the present invention. The handle 118 is then used to guide the valve holder 100 and prosthetic valve 1 along the pre-installed sutures to the native valve annulus.

During delivery of the valve, the pre-deployed deflector 112, with its umbrella shape, prevents entanglement of the commissure posts with the array of preinstalled sutures. Once the valve engages the native valve annulus, the handle can be removed by a single cut of suture 12 that secures the adapter 116 to the valve support body 110 and the adapter is pulled out of the central hole 202 of the valve support body 110. At the same time, the suture shield 242 of the adapter is also removed, exposing the sutures 11a, 11b, 11c that are arranged across gap 218 (see FIG. 14).

Figure 15:
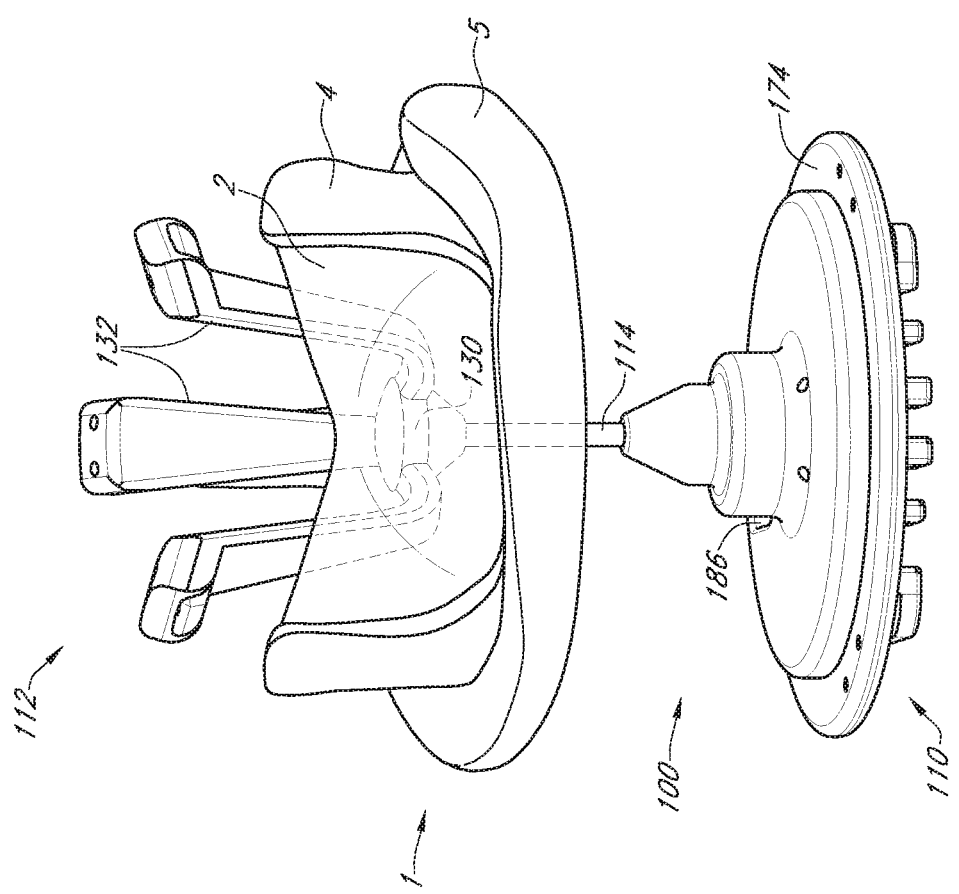
FIG. 15 shows a perspective view of the valve holder and prosthetic heart valve of FIG. 3 with the deflector in a collapsed state.

The pre-installed sutures may now be tied off to secure the prosthetic valve to the native valve annulus. Once completed, a member of the surgical team can make a single cut across the gap 218 to cut all three sutures 11a, 11b, 11c. The valve holder 100 can then be grasped with a tool, e.g., along the rib 188 between the tool openings 186 (see FIG. 5), and pulled away from the prosthetic valve. With reference to FIG. 15, as the valve holder is pulled from the prosthetic valve, the collapsible arms 132 of the deflector 112 invert, or fold backward, or flexibly bend, when being pulled through the leaflets 2 and the contact is soft enough to cause no damage to the prosthetic valve or leaflets. In this collapsed position, the central hub 130 is located axially between the free ends of the deflector arms 132 and the valve support body 110.

Figure 16:
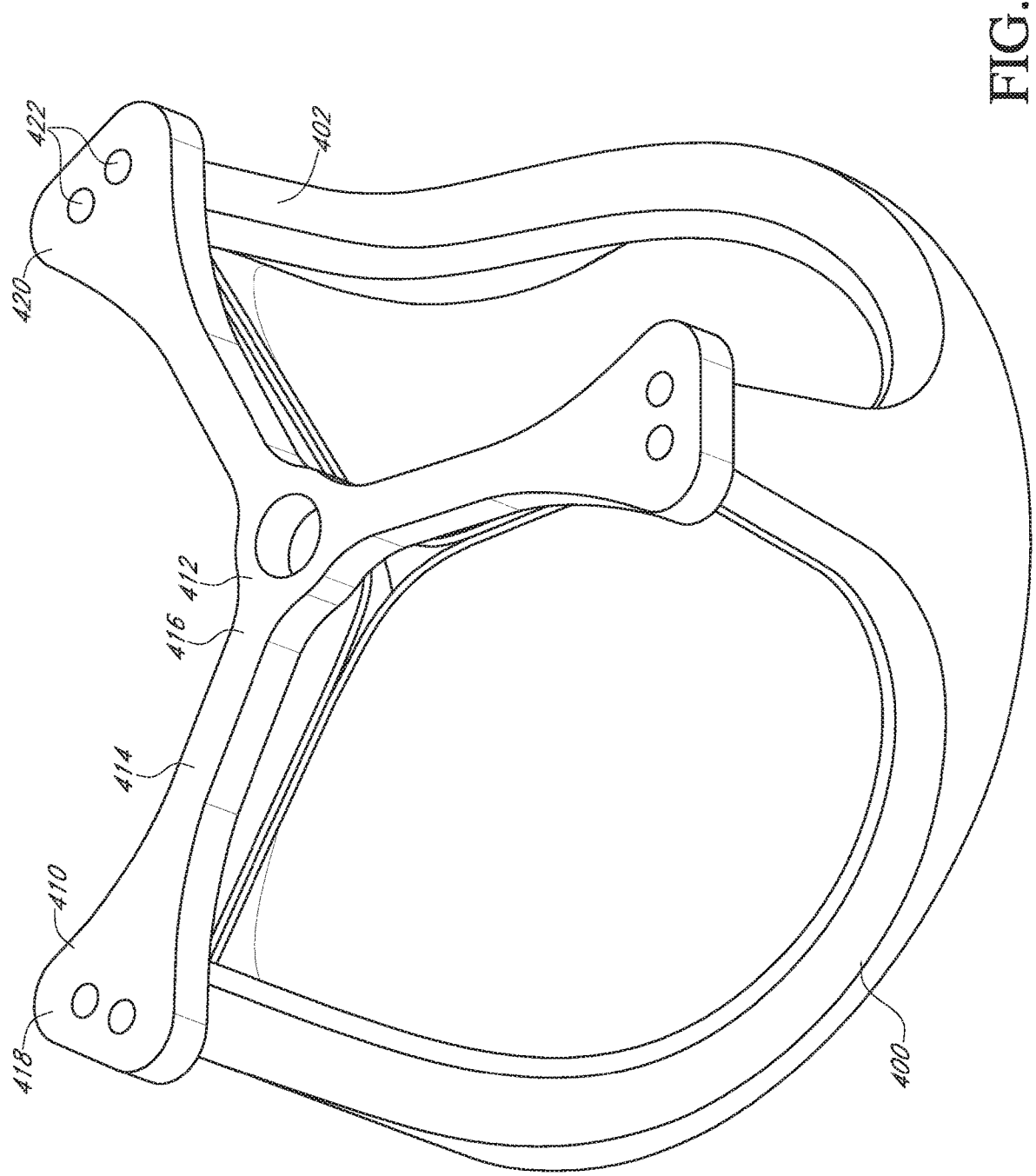
FIG. 16 shows a perspective view of a deflector and a prosthetic heart valve according to a modified embodiment of the invention.

With reference to FIG. 16, another embodiment of a deflector 410 mounted to a prosthetic heart valve 400 includes a central hub 412 and three generally radially extending arms 414. The deflector is a monolithic body made of a material, such as a soft silicone rubber or flexible polymer, which permits the arms to bend up and down.

A first end 416 of each arm is attached to the central hub 412 and each arm extends radially from the central hub to a free end 418. The arms are thin for most of their length, then gradually widen at their free ends to form attachment portions 420. A pair of suture holes 422 are formed through each attachment portion. Sutures may be used to attach the arms to the tips of the commissure posts 402 of the valve 400 as in the first embodiment. It will be appreciated that the deflector 410 may be substituted for the deflector 112 of the first embodiment, or other deflectors described in this application.

Figure 17:
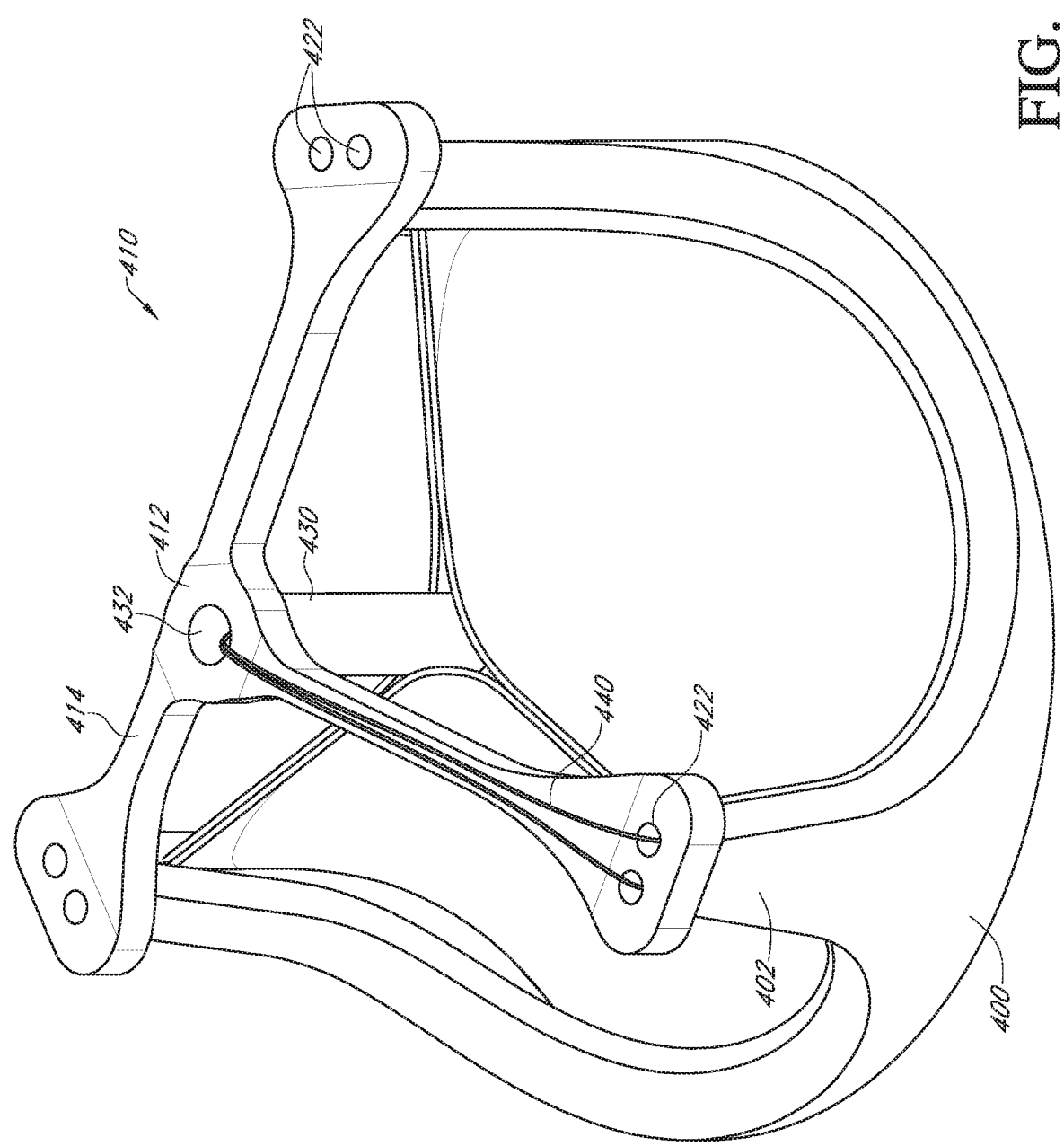
FIG. 17 shows a perspective view of a deflector and a prosthetic heart valve according to a further modified embodiment of the invention.

With reference to FIG. 17, in another embodiment, the central hub 412 of deflector 410 is tubular to form a central post 430 extending down toward the inflow end of the valve 400. A hole 432 passes through the central post toward the inflow end of the valve. In an alternative embodiment, a suture 440 may be routed up through the post 430 and radially along an arm 414 to a first of the pair of suture holes 422, then passed through the first hole and into the tip of the commissure post 402. The suture is passed back out of the tip and through the second hole of the pair of suture holes 422, along the arm radially inward to the hub 412 and routed back down the hole 432 to be attached on the inflow side of the valve. For example, the sutures 440 may pass through an opening or one of several openings in the conical member 178 or at a cylindrical base 190 next to the conical member (see FIG. 9). One end of the suture 440 may then be routed through the sewing ring 5 of the prosthetic valve and knotted at one of the pair of suture holes 175a in the support body 110 of the first embodiment. The other end of the suture 440 may be routed through the sewing ring 5, and through the other one of the pair of suture holes 175a, and routed through the suture tunnels 214a, 214b, 214c and the suture supports 212a, 212b as desired. Additional sutures are routed in a similar manner to the other two commissure posts 402.

Figure 18:
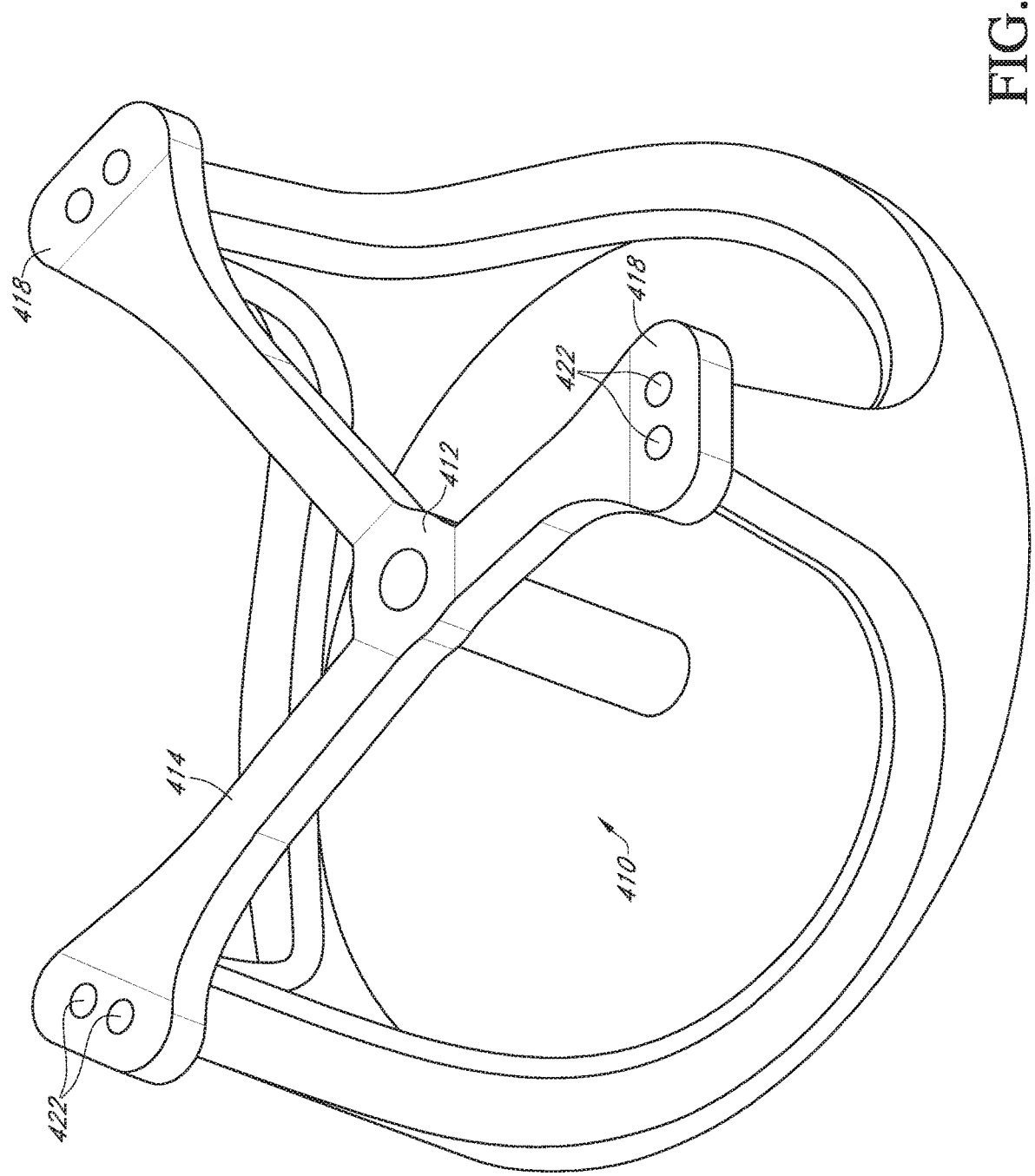
FIG. 18 shows a perspective view of the deflector and prosthetic heart valve of FIG. 17 with the deflector in a partially collapsed state and the valve leaflets removed to better view the other parts.

FIG. 17 shows the deflector 410 in a tented shape with the arms 414 bent at each of their ends near the central hub 412 and near the suture holes 422. The arms may also bend anywhere between the ends. FIG. 18 shows the deflector 410 in a partially collapsed shape wherein the central hub 412 is located axially below the free ends 418 of the deflector arms 414. The valve leaflets are removed in FIG. 18 to better view the other parts.

Figure 19:
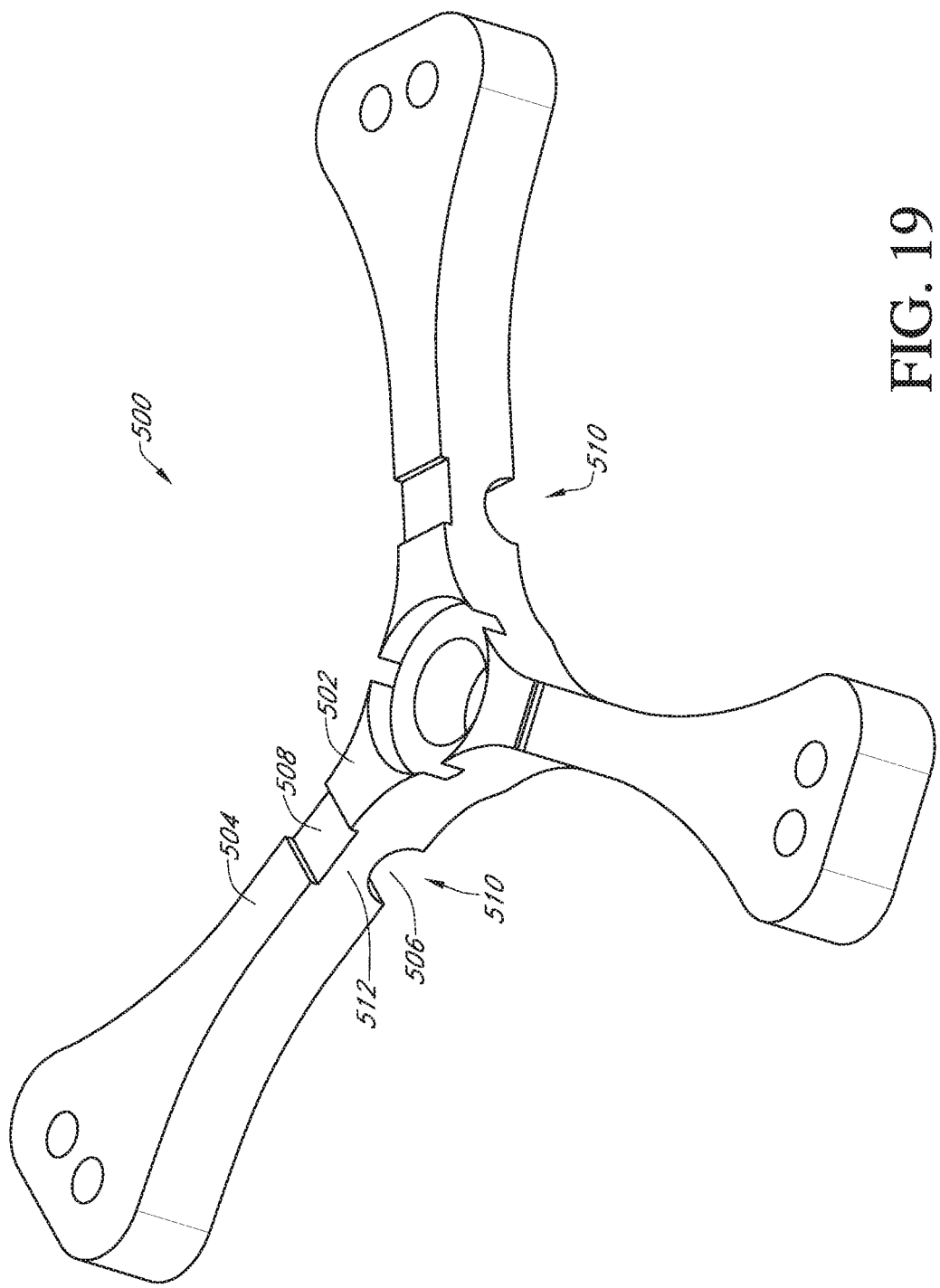
FIG. 19 shows a perspective view of a deflector according to a modified embodiment of the invention.

With reference to FIG. 19 another embodiment of a deflector 500 has a living hinge 510. The deflector has a central hub 502 and three generally radially extending arms 504. Each arm has a concavely curved notch 506 extending transversely fully across a bottom side of the arm to form the living hinge 510. A cornered recess 508 may also be formed in a top side of each arm, directly above the notch 506, leaving a thin rib 512 where bending or folding of each arm can occur. Alternatively, the concavely curved notch can be on the top side and the cornered recess can be on the bottom side, or only one side can have a notch or recess, or both sides can have notches or recesses.

Figure 20:
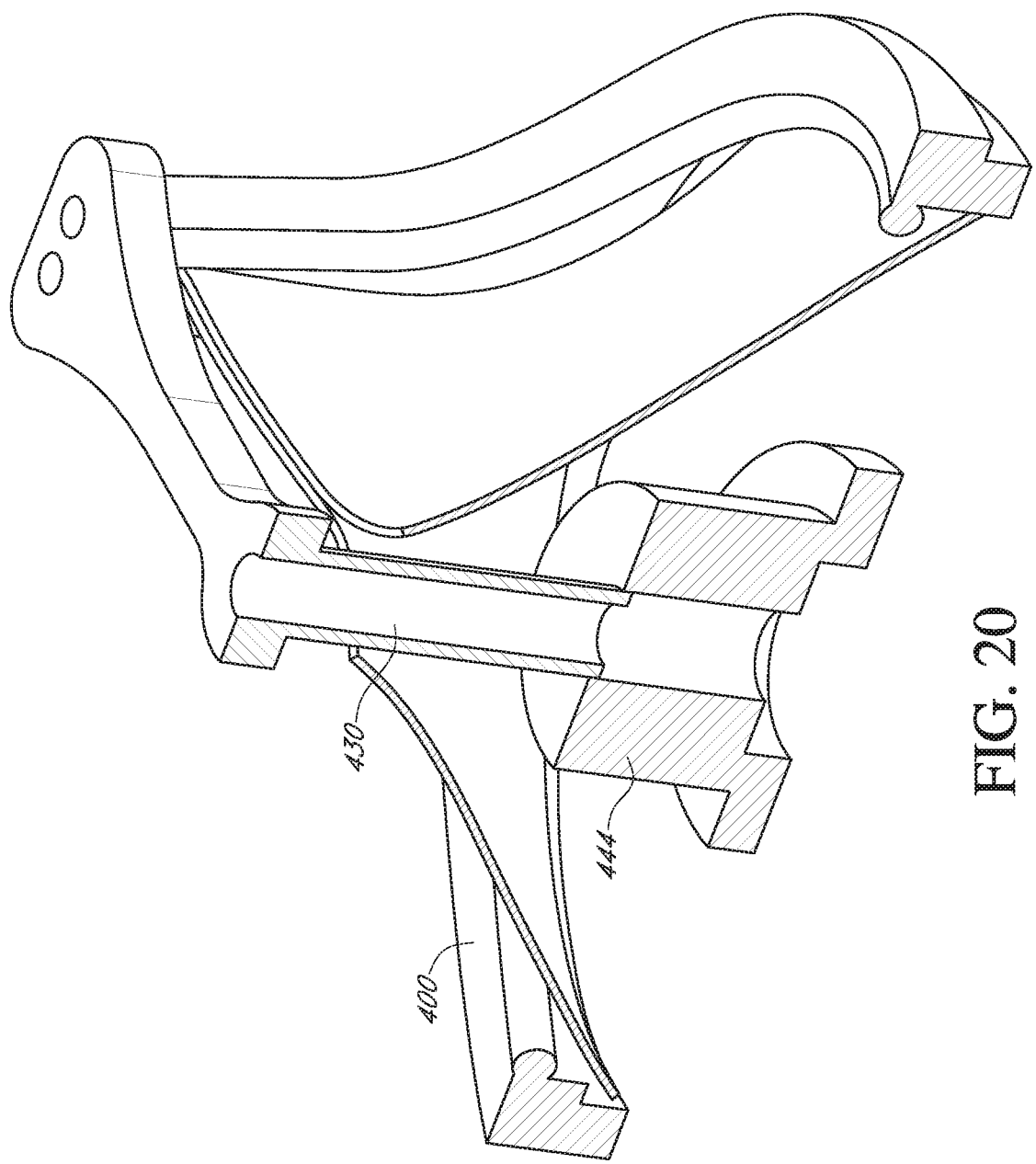
FIG. 20 shows a perspective view of a deflector, a handle adapter and a prosthetic heart valve according to an alternative embodiment of the invention.
Figure 21:
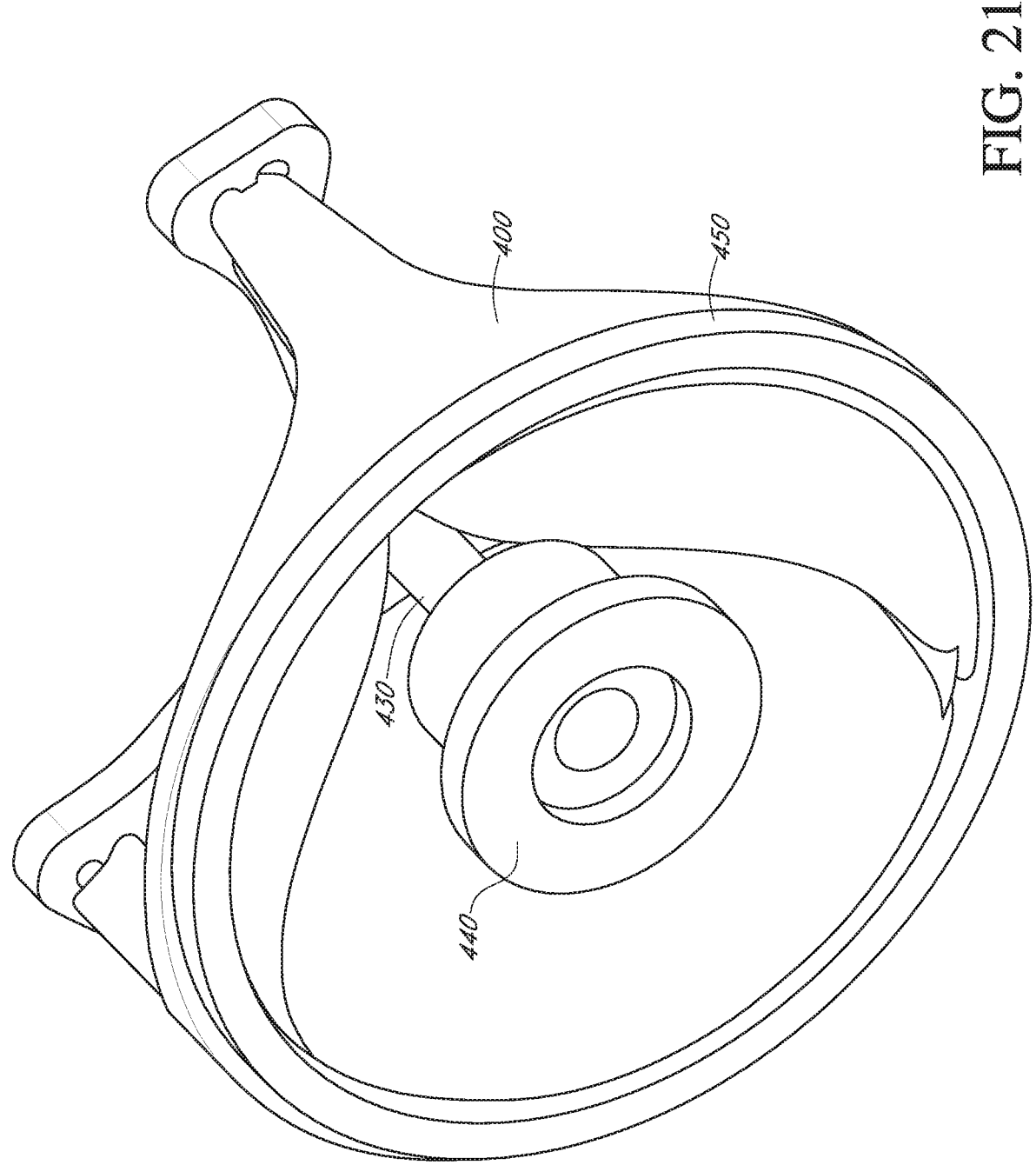
FIG. 21 shows a perspective view of a deflector, an adapter, and a prosthetic heart valve mounted to a ring according to another alternative embodiment of the invention.

In some situations, it may be desirable to move the deflector from an untented position to a tented position while attached to the prosthetic valve. With reference to FIG. 20, the central post 430 of the deflector is secured to a handle adapter 444 (shown schematically). Such an adapter 444 may form part of a valve holder (not shown), such as described in U.S. Pat. No. 6,966,925, incorporated by reference herein, to permit movement and locking of the post and deflector 430 relative to the prosthetic valve 400. With reference to FIG. 21, in another embodiment, the prosthetic valve is mounted to a ring 450. The ring may be used for suture attachment for sutures routed through the central post 430 and/or the adapter 444.

It will be appreciated that several ways of routing sutures between the prosthetic valve 1 and the valve holder 100 are described herein for insuring that those sutures are removed together with the valve holder after the prosthetic valve is delivered to the native valve annulus and that suture routing for one embodiment may be used in other embodiments.

In other alternative embodiments, various different features from the different embodiments discussed above can also be combined into a single modified valve holder. In addition, various other modifications or alternative configurations can also be made to the valve holder according to the above described embodiments of the invention.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather, the scope of the disclosure is defined by the following claims.

What is claimed is:

1. A prosthetic heart valve holder comprising:
   a deflector having a hub and a plurality of arms extending radially outwardly from the hub, each of the arms having a first end connected to the hub and a free second end positioned radially outwardly from the hub;
   a valve support body; and
   a post extending between and connecting the valve support body and the hub, wherein an outer width of the hub is greater than an outer width of the post;
   wherein the arms are deflectable axially relative to the hub, such that in a first configuration the second ends of the arms are positioned closer axially to the valve support body than the hub is to the valve support body, and in a second configuration the second ends of the arms are positioned farther away axially from the valve support body than the hub is to the valve support body.

2. The prosthetic heart valve holder of claim 1, wherein the deflector comprises at least three arms.

3. The prosthetic heart valve holder of claim 1, wherein an end of the post is insertable into the hub of the deflector.

4. The prosthetic heart valve holder of claim 1, wherein the post comprises a solid pin.

5. The prosthetic heart valve holder of claim 1, wherein the post is molded or press-fit to the hub of the deflector.

6. The prosthetic heart valve holder of claim 1, wherein an axial distance between the hub of the deflector and the valve support body remains fixed.

7. The prosthetic heart valve holder of claim 1, further comprising an adaptor that is detachably connectable to a side of the valve support body opposite the post and the deflector, wherein the adaptor comprises a suture shield for covering sutures which connect a prosthetic heart valve to the prosthetic heart valve holder.

8. The prosthetic heart valve holder of claim 1, further comprising a handle that is detachably connectable to a side of the valve support body opposite the post.

9. A prosthetic heart valve holder comprising:
a deflector having a hub and a plurality of arms extending radially outwardly from the hub, each of the arms having a first end connected to the hub and a free second end positioned radially outwardly from the hub;
a valve support body; and
a post extending between and connecting the valve support body and the hub, wherein each of the arms remains entirely spaced apart from the post;
wherein the arms are deflectable axially relative to the hub, such that in a first configuration the second ends of the arms are positioned closer axially to the valve support body than the hub is to the valve support body, and in a second configuration the second ends of the arms are positioned farther away axially from the valve support body than the hub is to the valve support body.

10. The prosthetic heart valve holder of claim 9, wherein the deflector comprises at least three arms.

11. The prosthetic heart valve holder of claim 9, wherein the hub is positioned between the post and each of the arms and prevents the arms from contacting the post.

12. The prosthetic heart valve holder of claim 9, wherein each of the arms defines a transversely extending notch that forms a living hinge.

13. The prosthetic heart valve holder of claim 9, wherein the post comprises a solid pin.

14. The prosthetic heart valve holder of claim 9, wherein the post is molded or press-fit to the hub of the deflector.

15. The prosthetic heart valve holder of claim 9, wherein an axial distance between the hub of the deflector and the valve support body remains fixed.

16. The prosthetic heart valve holder of claim 9, further comprising an adaptor that is detachably connectable to a side of the valve support body opposite the post and the deflector, wherein the adaptor comprises a suture shield for covering sutures which connect a prosthetic heart valve to the prosthetic heart valve holder.

17. The prosthetic heart valve holder of claim 9, further comprising a handle that is detachably connectable to a side of the valve support body opposite the post.

18. A prosthetic heart valve holder comprising:
a deflector having a hub and a plurality of arms extending radially outwardly from the hub, each of the arms having a first end connected to the hub and a free second end positioned radially outwardly from the hub;
a valve support body; and
a post extending between and connecting the valve support body and the hub;
wherein the arms are deformable axially relative to the hub, such that in a first configuration the second ends of the arms are positioned closer axially to the valve support body than the hub is to the valve support body, and in a second configuration the second ends of the arms are positioned farther away axially from the valve support body than the hub is to the valve support body.

19. The prosthetic heart valve holder of claim 18, wherein the arms of the deflector comprise a material with a durometer in the range of shore A30 to shore A70.

20. The prosthetic heart valve holder of claim 18, wherein each of the arms defines a transversely extending notch that forms a living hinge.

* * * * *